(12) United States Patent
Dhanak et al.

(10) Patent No.: US 7,026,349 B2
(45) Date of Patent: Apr. 11, 2006

(54) SULFONAMIDES

(75) Inventors: Dashyant Dhanak, King of Prussia, PA (US); Timothy F. Gallagher, Collegeville, PA (US); Steven D. Knight, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/477,068

(22) PCT Filed: May 7, 2002

(86) PCT No.: PCT/US02/14543

§ 371 (c)(1),
(2), (4) Date: Nov. 7, 2003

(87) PCT Pub. No.: WO02/089792

PCT Pub. Date: Nov. 14, 2002

(65) Prior Publication Data

US 2004/0152906 A1    Aug. 5, 2004

Related U.S. Application Data

(60) Provisional application No. 60/289,327, filed on May 7, 2001.

(51) Int. Cl.
*A61K 31/40* (2006.01)
*C07D 207/12* (2006.01)

(52) U.S. Cl. ........................... 514/424; 548/541
(58) Field of Classification Search ............... 548/541; 514/424

See application file for complete search history.

(56) References Cited

FOREIGN PATENT DOCUMENTS

| JP | 06-329626 A | 11/1994 |
|----|-------------|---------|
| WO | WO98/27081 | 6/1998 |
| WO | WO99/38845 | 8/1999 |

OTHER PUBLICATIONS

Golub et al., Science, vol. 286, Oct. 15, 1999, pp. 531-537.*

* cited by examiner

*Primary Examiner*—Laura L. Stockton
(74) *Attorney, Agent, or Firm*—Linda E. Hall; Stephen A Venetianer; Charles M Kinzig

(57) ABSTRACT

The present invention relates to sulfonamides, pharmaceutical compositions containing them, and their use as antagonists of urotensin II.

10 Claims, No Drawings

SULFONAMIDES

This application is a 371 of International Application PCT/US02/14543, filed 7 May 2002; which claims the benefit of U.S. Provisional Application No. 60/289,327, filed 7 May 2001.

FIELD OF THE INVENTION

The present invention relates to sulfonamides, pharmaceutical compositions containing them and their use as urotensin II antagonists

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, norepinephrine, all function via an interaction with specific G-protein coupled receptors (GPCR). Urotensin-II, represents a novel member of this neurohumoral axis.

In the fish, this peptide has significant hemodynamic and endocrine actions in diverse end-organ systems and tissues: smooth muscle contraction
- both vascular and non-vascular in origin including smooth muscle preparations from the gastrointestinal tract and genitourinary tract. Both pressor and depressor activity has been described upon systemic administration of exogenous peptide osmoregulation:
- effects which include the modulation of transepithelial ion ($Na^+$, $Cl^-$) transport. Although a diuretic effect has been described, such an effect is postulated to be secondary to direct renovascular effects (elevated GFR)

metabolism:
- urotensin-II influences prolactin secretion and exhibits a lipolytic effect in fish (activating triacylglycerol lipase resulting in the mobilization of non-esterified free fatty acids)
- (Pearson, et. al. *Proc. Natl. Acad. Sci. (U.S.A.)* 1980, 77, 5021; Conlon, et. al. *J. Exp. Zool.* 1996, 275, 226.)

In studies with human Urotensin-II it was found that it:
was an extremely potent and efficacious vasoconstrictor
exhibited sustained contractile activity that was extremely resistant to wash out
had detrimental effects on cardiac performance (myocardial contractility)

Human Urotensin-II was assessed for contractile activity in the rat-isolated aorta and was shown to be the most potent contractile agonist identified to date. Based on the in vitro pharmacology and in vivo hemodynamic profile of human Urotensin-II it plays a pathological role in cardiovascular diseases characterized by excessive or abnormal vasoconstriction and myocardial dysfunction. (Ames et. al. *Nature* 1999, 401, 282; Douglas & Ohlstein (2001). Trends Cardiovasc. Med., 10: in press).

Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma, (Hay D W P, Luttmann M A, Douglas S A: 2000, Br J Pharmacol: 131; 10–12) neurogenic inflammation and metabolic vasculopathies all of which are characterized by abnormal vasoconstriction and/or myocardial dysfunction. Urotensin antagonists may provide end organ protection in hypersensitive cohorts in addition to lowering blood pressure.

Since U-II and GPR14 are both expressed within the mammalian CNS (Ames et. al. *Nature* 1999, 401, 282), they also may be useful in the treatment of addiction, schizophrenia, cognitive disorders/Alzheimers disease, (Gartlon J. Psychopharmacology (Berl) 2001 June; 155(4):426–33), impulsivity, anxiety, stress, depression, pain, migraine, neuromuscular function, parkinsons, movement disorders, sleep-wake cycle, and incentive motivation (Clark et al. *Brain Research* 923 (2001) 120–127.

Functional U-II receptors are expressed in rhabdomyosarcomas cell lines and therefore may have oncological indications. Urotensin may also be implicated in various metabolic diseases such as diabetes (Ames et. al. *Nature* 1999, 401, 282, Nothacker et al., *Nature Cell Biology* 1: 383–385, 1999) and in various gastrointestinal disorders, bone, cartilage, and joint disorders (e.g. arthritis and osteoporosis); and genito-urinary disorders. Therefore, these compounds may be useful for the prevention (treatment) of gastric reflux, gastric motility and ulcers, arthritis, osteoporosis and urinary incontinence.

SUMMARY OF THE INVENTION

In one aspect this invention provides for sulfonamides and pharmaceutical compositions containing them.

In a second aspect, this invention provides for the use of sulfonamides as antagonists of urotensin II, and as inhibitors of urotensin II.

In another aspect, this invention provides for the use of sulfonamides for treating conditions associated with urotensin II imbalance.

In yet another aspect, this invention provides for the use of sulfonamides for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases, arthritis and other inflammatory diseases, fibrosis (e.g. pulmonary fibrosis), sepsis, atherosclerosis, dyslipidemia, addiction, schizophrenia, cognitive disorders/Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and $α_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula (I):

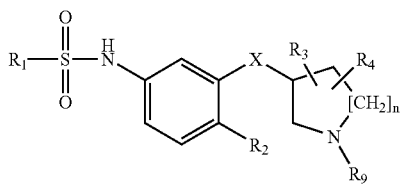

Formula (I)

wherein:
R$_1$ is phenyl substituted or unsubstituted by one, two, three, four or five of any of the following: halogen, CF$_3$, OCF$_3$, SCF$_3$, NO$_2$, CN, C$_{1-6}$ alkyl, C$_{1-6}$ alkoxy, NR$_5$R$_6$, CONR$_7$R$_8$, SC$_{1-6}$ alkyl, CO$_2$(C$_{1-6}$ alkyl), C$_{1-6}$ alkyl-CO$_2$ (C$_{1-6}$ alkyl);
R$_2$ is hydrogen, halogen, CF$_3$, CN or C$_{1-4}$ alkyl;
R$_3$, R$_4$, R$_7$, and R$_8$ are independently hydrogen, C$_{1-6}$ alkyl, or benzyl;
R$_5$, R$_6$, and R$_9$, are independently hydrogen or C$_{1-6}$ alkyl;
X is O, S, or CH$_2$;
n is 1;
or a pharmaceutically acceptable salt thereof.

When used herein, the term "alkyl" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms 'halogen' and 'halo' include fluorine, chlorine, bromine and iodine, and fluoro, chloro, bromo and iodo, respectively.

The compounds of the present invention may contain one or more asymmetric carbon atoms and may exist in racemic and optically active form. All of these compounds and their diastereoisomers are contemplated to be within the scope of the present invention.

Preferably R$_1$ is phenyl substituted or unsubstituted by one, two, three, four, or five of any of the following: halogen, CF$_3$, OCF$_3$, CN, C$_{1-6}$ alkyl, C$_{1-6}$ alkoxy, CO$_2$(C$_{1-6}$ alkyl), C$_{1-6}$ alkyl-CO$_2$(C$_{1-6}$ alkyl), or NO$_2$.
Preferably R$_2$ is hydrogen, halogen, CF$_3$, or C$_{1-4}$ alkyl. More preferably R$_2$ is halogen or CF$_3$.
Preferably R$_3$ is hydrogen.
Preferably R$_4$ is hydrogen.
Preferably R$_9$ is hydrogen or C$_{1-6}$ alkyl.
Preferably X is O.

Preferred compounds are:
(R)-N-[4-Chloro-3-(1-methyl-3-pyrrolidinyloxy)-phenyl]-2,4,5-triimethoxybenzenesulfonamide hydrochloride;
(±)-N-[4-Chloro-3-(1-methyl-3-pyrrolidinyloxy)-phenyl]-2-bromo-4,5-dimethoxybenzenesulfonamide;
(±)-N-[4-Chloro-3-(1-ethyl-3-pyrrolidinyloxy)-phenyl]-3,4-dimethoxybenzenesulfonamide;
(S)-N-[4-Chloro-3-(1-methyl-3-pyrrolidinyloxy)-phenyl]-3,4-dimethoxybenzenesulfonamide;
(R)-N-[4-Chloro-3-(1-methyl-3-pyrrolidinyloxy)-phenyl]-3,4-dimethoxybenzenesulfonamide;
(R)-N-[4-Chloro-3-(1-methyl-3-pyrrolidinyloxy)-phenyl]-2-bromo-4,5-dimethoxybenzenesulfonamide;
(R)-N-[4-Chloro-3-(1-methyl-3-pyrrolidinyloxy)-phenyl]-2,6-dichloro-4-trifluoromethylbenzene-sulfonamide;
(±)-N-[4-Chloro-3-(1-methyl-3-pyrrolidinyloxy)-phenyl]-3,4-dimethoxybenzenesulfonamide;
(S)-N-[4-Chloro-3-(1-methyl-3-pyrrolidinyloxy)-phenyl]-2,6-dichloro-4-trifluoromethylbenzene-sulfonamide;
2-Bromo-N-[4-chloro-3-((S)-1-methyl-pyrrolidin-3-yloxy)-phenyl]-4,5-dimethoxybenzenesulfonamide;
4-Bromo-2-chloro-N-[4-chloro-3-((R)-1-methyl-pyrrolidin-3-yloxy)-phenyl]-5-methoxybenzenesulfonamide;
2,4-Dibromo-N-[4-chloro-3-((R)-1-methyl-pyrrolidin-3-yloxy)-phenyl]-5-methoxybenzenesulfonamide;
(R)-N-[4-Chloro-3-(1-ethyl-3-pyrrolidinyloxy)-phenyl]-3,4-dimethoxybenzenesulfonamide;
(R)-N-[4-Chloro-3-(1-ethyl-3-pyrrolidinyloxy)-phenyl]-2-bromo-4,5-dimethoxybenzenesulfonamide;
(R)-N-[4-Chloro-3-(1-methyl-3-pyrrolidinyloxy)-phenyl]-2-chloro-4,5-dimethoxybenzenesulfonamide;
(R)-N-[4-Chloro-3-(1-methyl-3-pyrrolidinyloxy)-phenyl]-2-methyl-4,5-dimethoxybenzenesulfonamide;
(±)-N-[4-Chloro-3-(1-isopropyl-3-pyrrolidinyloxy)-phenyl]-3,4-dimethoxybenzenesulfonamide;
(±)-N-[4-Chloro-3-(1-isopropyl-3-pyrrolidinyloxy)-phenyl]-2-bromo-4,5-dimethoxybenzenesulfonamide;
(R)-N-[4-Chloro-3-(1-isopropyl-3-pyrrolidinyloxy)-phenyl]-2-bromo-4,5-dimethoxybenzenesulfonamide;
(R)-N-[4-Chloro-3-(1-methyl-3-pyrrolidinyloxy)-phenyl]-2-methyl-4-bromobenzenesulfonamide;
(R)-N-[4-Chloro-3-(1-isopropyl-3-pyrrolidinyloxy)-phenyl]-3,4-dimethoxybenzenesulfonamide;
(R)-N-[4-Chloro-3-(1-methyl-3-pyrrolidinyloxy)-phenyl]-2,4,5-trichlorobenzenesulfonamide;
(R)-N-[4-Chloro-3-(1-methyl-3-pyrrolidinyloxy)-phenyl]-2,3,4,5,6-pentamethylbenzenesulfonamide;
(R)-N-[4-Chloro-3-(1-methyl-3-pyrrolidinyloxy)-phenyl]-2-methoxy-5-bromobenzenesulfonamide;
(R)-N-[4-Chloro-3-(1-methyl-3-pyrrolidinyloxy)-phenyl]-4-(methylpropionate)benzenesulfonamide;
(R)-N-[4-Chloro-3-(1-methyl-3-pyrrolidinyloxy)-phenyl]-2,5-difluoro-4-bromobenzenesulfonamide;
(R)-N-[4-Chloro-3-(1-methyl-3-pyrrolidinyloxy)-phenyl]-2,3,6-trimethyl-4-methoxybenzenesulfonamide;
(R)-N-[4-Chloro-3-(1-methyl-3-pyrrolidinyloxy)-phenyl]-2,3,4-trichlorobenzenesulfonamide;
(R)-N-[4-Chloro-3-(1-methyl-3-pyrrolidinyloxy)-phenyl]-2,3,5,6-tetramethylbenzenesulfonamide;
(R)-N-[4-Chloro-3-(1-methyl-3-pyrrolidinyloxy)-phenyl]-4-isopropylbenzenesulfonamide;
(R)-N-[4-Chloro-3-(1-methyl-3-pyrrolidinyloxy)-phenyl]-4-ethylbenzenesulfonamide;
(R)-N-[4-Chloro-3-(1-methyl-3-pyrrolidinyloxy)-phenyl]-2-chloro-4-cyanobenzenesulfonamide;
(R)-N-[4-Chloro-3-(1-methyl-3-pyrrolidinyloxy)-phenyl]-2,4-dichloro-6-methylbenzenesulfonamide;
(R)-N-[4-Chloro-3-(1-methyl-3-pyrrolidinyloxy)-phenyl]-2,5-difluoro-3,6-dibromobenzenesulfonamide;
(R)-N-[4-Chloro-3-(1-methyl-3-pyrrolidinyloxy)-phenyl]-2-trifluoromethoxy-4-bromobenzenesulfonamide;
(R)-N-[4-Chloro-3-(1-methyl-3-pyrrolidinyloxy)-phenyl]-3-fluorobenzenesulfonamide;
(R)-N-[4-Chloro-3-(1-methyl-3-pyrrolidinyloxy)-phenyl]-4-butylbenzenesulfonamide;
(R)-N-[4-Chloro-3-(1-methyl-3-pyrrolidinyloxy)-phenyl]-2,4-difluoro-5-bromobenzenesulfonamide;
(R)-N-[4-Chloro-3-(1-methyl-3-pyrrolidinyloxy)-phenyl]-2,4-difluoro-5-chlorobenzenesulfonamide;

(R)-N-[4-Chloro-3-(1-methyl-3-pyrrolidinyloxy)-phenyl]-3-fluoro-4-methoxybenzenesulfonamide;
(R)-N-[4-Chloro-3-(1-methyl-3-pyrrolidinyloxy)-phenyl]-2chloro-4,5-difluorobenzenesulfonamide;
(R)-N-[4-Chloro-3-(1-methyl-3-pyrrolidinyloxy)-phenyl]-2,5-difluoro-4chlorobenzenesulfonamide;
(R)-N-[4-Chloro-3-(1-methyl-3-pyrrolidinyloxy)-phenyl]-3-nitro-4-chlorobenzenesulfonamide;
(R)-N-[4-Chloro-3-(1-methyl-3-pyrrolidinyloxy)-phenyl]-2,6-dimethyl-4-bromobenzenesulfonamide;
(R)-N-[4-Chloro-3-(1-methyl-3-pyrrolidinyloxy)-phenyl]-3,4-dibromobenzenesulfonamide;
(R)-N-[4-Chloro-3-(1-methyl-3-pyrrolidinyloxy)-phenyl]-2,4,6-trichlorobenzenesulfonamide;
(R)-N-[4-Chloro-3-(1-methyl-3-pyrrolidinyloxy)-phenyl]-5-fluoro-4-methoxy-2-trifluoromethylbenzenesulfonamide;
(R)-N-[4-Chloro-3-(1-methyl-3-pyrrolidinyloxy)-phenyl]-3,5-difluoro-4-methoxy-2-methylbenzenesulfonamide;
(R)-N-[4-Chloro-3-(1-methyl-3-pyrrolidinyloxy)-phenyl]-6-bromo-2,3-difluoro-4-methoxybenzenesulfonamide;
(R)-N-[4-Chloro-3-(1-methyl-3-pyrrolidinyloxy)-phenyl]-4,5-dimethoxy-2-trifluoromethylbenzenesulfonamide;
(R)-N-[4-Chloro-3-(1-methyl-3-pyrrolidinyloxy)-phenyl]-2,6-dichloro-4,5-dimethoxybenzenesulfonamide;
(R)-N-[4-Chloro-3-(1-methyl-3-pyrrolidinyloxy)-phenyl]-4-fluoro-2-trifluoromethylbenzenesulfonamide;
(R)-N-[4-Chloro-3-(1-methyl-3-pyrrolidinyloxy)-phenyl]-2,4,6-trifluorobenzenesulfonamide;
3,4-Dimethoxy-N-[4-methyl-3-((R)-1-methyl-pyrrolidin-3-yloxy)-phenyl]-benzenesulfonamide;
2-Bromo-4,5-dimethoxy-N-[4-methyl-3-((R)-1-methyl-pyrrolidin-3-yloxy)-phenyl]-benzenesulfonamide;
2-Chloro-4,5-dimethoxy-N-[4-methyl-3-((R)-1-methyl-pyrrolidin-3-yloxy)-phenyl]-benzenesulfonamide;
4,5-Dimethoxy-2-methyl-N-[4-methyl-3-((R)-1-methyl-pyrrolidin-3-yloxy)-phenyl]-benzenesulfonamide;
4-Bromo-2-chloro-5-methoxy-N-[4-methyl-3-((R)-1-methyl-pyrrolidin-3-yloxy)-phenyl]-benzenesulfonamide;
2-Bromo-4,5-dimethoxy-N-[4-methyl-3-((S)-1-methyl-pyrrolidin-3-yloxy)-phenyl]-benzenesulfonamide;
N-[4-Chloro-3-((R)-pyrrolidin-3-yloxy)-phenyl]-2-bromo-3,4-dimethoxybenzenesulfonamide;
(±)-N-[4-Chloro-3-(3-pyrrolidinyloxy)-phenyl]-3,4-dimethoxybenzenesulfonamide;
(R)-N-[4-Chloro-3-(3-pyrrolidinyloxy)-phenyl]-3,4-dimethoxybenzenesulfonamide;
(±)-N-[4-Chloro-3-(3-pyrrolidinyloxy)-phenyl]-2-bromo-4,5-dimethoxybenzenesulfonamide;
2-Chloro-4,5-dimethoxy-3-[((R)-1-methyl-pyrrolindin-3-yloxy)-4-trifluoromethyl-phenyl]-benzenesulfonamide;
2,6-Dichloro-[3-((R)-1-methyl-pyrrolidin-3-yloxy)-4-trifluoromethyl-phenyl]-4-trifluoromethylbenzenesulfonamide;
2-Bromo-4,5-dimethoxy-N-[3-(1-methyl-pyrrolidin-3-yloxy-4-trifluormethy-phenyl]-benzenesulfonamide;
3,4-Dimethoxy-N-[3-((R)-1-methyl-pyrrolidin-3-yloxy)-4-trifluoromethyl-phenyl]-benzenesulfonamide;
2,4,5-Trichloro-N-[3-((R)-1-methyl-pyrrolidin-3-yloxy)-4-trifluoromethyl-phenyl]-benzenesulfonamide;
2,3,4,5,6-Pentamethyl-N-[3-((R)-1-methyl-pyrrolidin-3-yloxy)-4-trifluoromethyl-phenyl]-benzenesulfonamide;
4-Bromo-2,5-difluoro-N-[3-((R)-1-methyl-pyrrolidin-3-yloxy)-4-trifluoromethyl-phenyl]-benzenesulfonamide;
2,3,4-Trichloro-N-[3-((R)-1-methyl-pyrrolidin-3-yloxy)-4-trifluoromethyl-phenyl]-benzenesulfonamide;
4-Isopropyl-N-[3-((R)-1-methyl-pyrrolidin-3-yloxy)-4-trifluoromethyl-phenyl]-benzenesulfonamide;
2,4-Dichloro-6-methyl-N-[3-((R)-1-methyl-pyrrolidin-3-yloxy)-4-trifluoromethyl-phenyl]-benzenesulfonamide;
3,4-Dibromo-N-[3-((R)-1-methyl-pyrrolidin-3-yloxy)-4trifluoromethyl-phenyl]-benzenesulfonamide;
2,4,6-Trichloro-N-[3-((R)-1-methyl-pyrrolidin-3-yloxy)-4-trifluoromethyl-phenyl]-benzenesulfonamide;
5-Bromo-2,4-difluoro-N-[3-((R)-1-methyl-pyrrolidin-3-yloxy)-4-trifluoromethyl-phenyl]-benzenesulfonamide;
5-Chloro-2,4-difluoro-N-[3-((R)-1-methyl-pyrrolidin-3-yloxy)-4trifluoromethyl-phenyl]-benzenesulfonamide;
4-Chloro-2,5-difluoro-N-[3-((R)-1-methyl-pyrrolidin-3-yloxy)-4-trifluoromethyl-phenyl]-benzenesulfonamide;
4-Methoxy-2,3,6-trimethyl-N-[3-((R)-1-methyl-pyrrolidin-3-yloxy)-4-trifluoromethyl-phenyl]-benzenesulfonamide;
3,5-Dimethoxy-2-methyl-N-[3-((R)-1-methyl-pyrrolidin-3-yloxy)-4-trifluoromethyl-phenyl]-benzenesulfonamide;
2,4-Dibromo-5-methoxy-N-[3-((R)-1-methyl-pyrrolidin-3-yloxy)-4-trifluoromethyl-phenyl]-benzenesulfonamide;
2-Bromo-5,6-difluoro-4-methoxy-N-[3-((R)-1-methyl-pyrrolidin-3-yloxy)-4-trifluoromethyl -phenyl]-benzenesulfonamide;
4,5-Dimethoxy-2-trifluoromethyl-N-[3-((R)-1-methyl-pyrrolidin-3-yloxy)-4-trifluoromethyl-phenyl]-benzenesulfonamide;
2,4,5-Trimethoxy-N-[3-((R)-1-methyl-pyrrolidin-3-yloxy)-4-trifluoromethyl-phenyl]-benzenesulfonamide; and
4-Bromo-2,6-dimethyl-N-[3-((R)-1-methyl-pyrrolidin-3-yloxy)-4-trifluoromethyl-phenyl]-benzenesulfonamide.

More preferred compounds are:
(R)-N-[4-Chloro-3-(1-methyl-3-pyrrolidinyloxy)-phenyl]-2-bromo-4,5-dimethoxybenzenesulfonamide;
(R)-N-[4-Chloro-3-(1-methyl-3-pyrrolidinyloxy)-phenyl]-2,6-dichloro-4-trifluoromethylbenzenesulfonamide;
(R)-N-[4-Chloro-3-(1-methyl-3-pyrrolidinyloxy)-phenyl]-2-chloro-4,5-dimethoxybenzenesulfonamide;
(R)-N-[4-Chloro-3-(1-methyl-3-pyrrolidinyloxy)-phenyl]-2,3,6-trimethyl-4-methoxybenzenesulfonamide;
2-Bromo-4,5-dimethoxy-N-[3-((R)-1-methyl-pyrrolindin-3-yloxy)-4-trifluoromethyl-phenyl]-benzenesulfonamide;
2-Chloro-4,5-dimethoxy-N-[3-((R)-1-methyl-pyrrolindin-3-yloxy)-4-trifluoromethyl-phenyl]-benzenesulfonamide; and
2,6-Dichloro-[3-((R)-1-methyl-pyrrolidin-3-yloxy)-4-trifluoromethyl-phenyl]-4-trifluoromethylbenzenesulfonamide.

Compounds of Formula (I) may be prepared as outlined in Scheme 1.

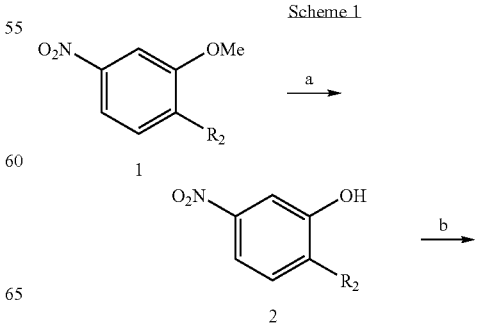

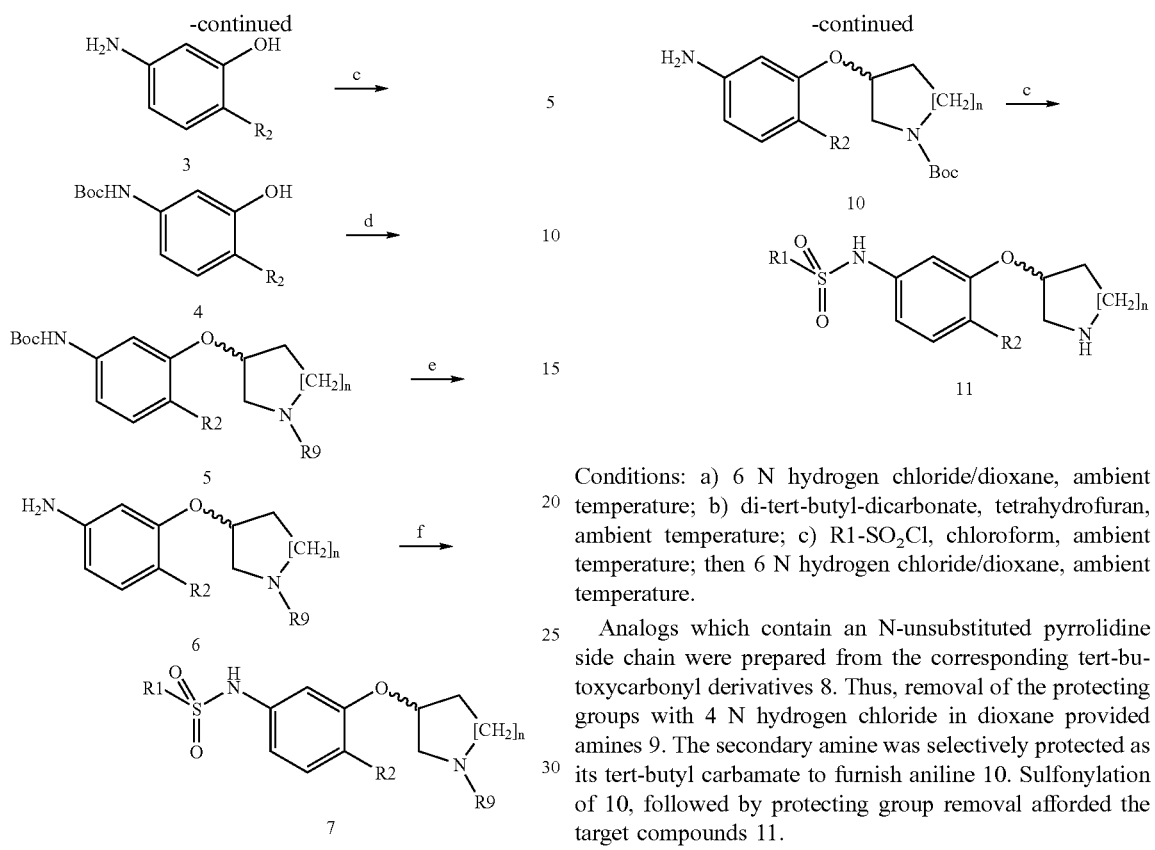

Conditions: a) 6 N hydrogen chloride/dioxane, ambient temperature; b) di-tert-butyl-dicarbonate, tetrahydrofuran, ambient temperature; c) R1-SO$_2$Cl, chloroform, ambient temperature; then 6 N hydrogen chloride/dioxane, ambient temperature.

Analogs which contain an N-unsubstituted pyrrolidine side chain were prepared from the corresponding tert-butoxycarbonyl derivatives 8. Thus, removal of the protecting groups with 4 N hydrogen chloride in dioxane provided amines 9. The secondary amine was selectively protected as its tert-butyl carbamate to furnish aniline 10. Sulfonylation of 10, followed by protecting group removal afforded the target compounds 11.

Compounds wherein R$_2$ is CF$_3$ may be prepared as follows:

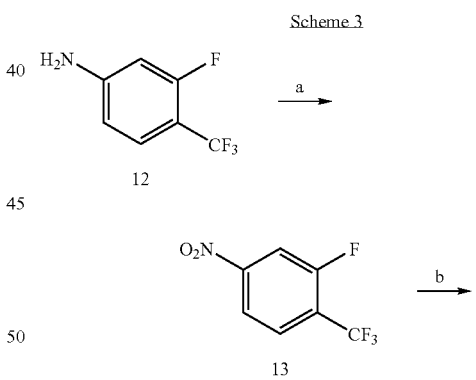

Conditions: a) 48% hydrogen bromide, acetic acid; b) hydrogen (50 psi), platinum on carbon, ethyl acetate; c) di-tent-butyldicarbonate, tetrahydrofuran, reflux; d) 1-R$_9$-pyrrolidin-3-ol, DIAD, triphenyephosphine, tetrahydrofuran, 0° C. to ambient temperature; e) 6 N HCl in dioxane; f) R1SO$_2$Cl, chloroform, ambient temperature.

For example, acid-mediated demethylation of anisoles 1 gave phenols 2. Hydrogenation of the nitro group provided anilines 3, which were subsequently protected as their tert-butoxycarbonyl carbamates 4. Alkylation of 4 with various alcohols using standard Mitsunobu conditions, followed by removal of the nitrogen protecting group afforded anilines 6. Subsequent sulfonylation of the anilines furnished the target compounds 7.

Analogs which contain an N-unsubstituted pyrrolidine side chain may be prepared according to scheme 2.

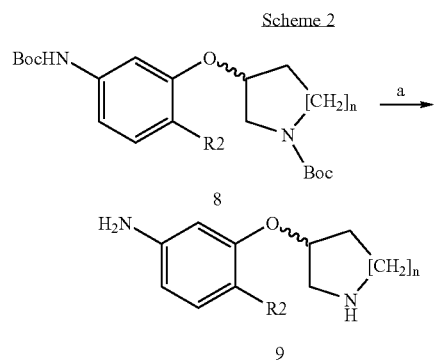

-continued

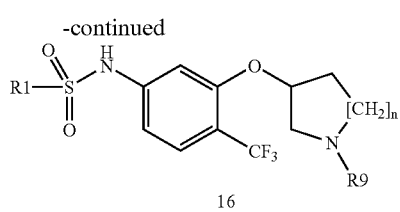

16

Conditions: a) 50% hydrogen peroxide, trifluoroacetic acetic acid, reflux; b) 1-R9-pyrrolidin-3-ol, sodium hydride, tetrahydrofuran, 0° C.; c) hydrogen (50 psi), platinum on carbon, ethyl acetate; d) R1-SO$_2$Cl, chloroform, room temperature.

For example, oxidation of aniline 12 gave nitrobenzene 13. Substitution of the aryl fluoride with various alcohols furnished the ethers 14. Hydrogenation of the nitro group provided anilines 15, which were subsequently sulfonylated with variuos sulfonyl chlorides to furnish the target compounds 16.

With appropriate manipulation, including the use of alternative nitrogen protecting group(s), the synthesis of the remaining compounds of Formula (I) was accomplished by methods analogous to those above and to those described in the Experimental section.

A number of optionally substituted benzenesulfonyl chlorides used in the synthesis of the title compounds were not available commercially and were prepared according to scheme 4. 2,4-Dibromo-5-methoxybenzenesulfonyl chloride was prepared as described in WO9838182.

Scheme 4

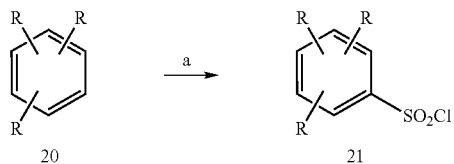

Substituted benzenes 20 were treated with chlorosulfonic acid to furnish the desired sulfonyl chlorides 21.

Conditions: a) chlorosulfonic acid, dichloromethane, 0° C. to ambient temperature.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

These sulphonamide analogs may be used for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases, arthritis and other inflammatory diseases, fibrosis (e.g. pulmonary fibrosis), sepsis, atherosclerosis, dyslipidemia, addiction, schizophrenia, cognitive disorders/Alzheimers disease, impulsivity, anxiety, stress, depression, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and α$_1$-adrenoceptor antagonists.

No unacceptable toxicological effects are expected when compounds of the invention are administered in accordance with the present invention.

The biological activity of the compounds of Formula (I) are demonstrated by the following tests:

Radioligand Binding:

HEK-293 cell membranes containing stable cloned human and rat GPR-14 (20 ug/assay) were incubated with 200 pM [125I] h-U-II (200 Ci/mmol$^{-1}$ in the presence of increasing concentrations of test compounds in DMSO (0.1 nM to 10 uM), in a final incubation volume of 200 ul (20 mM Tris-HCl, 5 mM MgCl2). Incubation was done for 30 minutes at room temperature followed by filtration GF/B filters with Brandel cell harvester. $^{125}$I labeled U-II binding was quantitated by gamma counting. Nonspecific binding was defined by $^{125}$I U-II binding in the presence of 100 nM of unlabeled human U-II. Analysis of the data was performed by nonlinear least square fitting.

Ca$^{2+}$-Mobilization:

A microtitre plate based Ca$^{2+}$-mobilization FLIPR assay (Molecular Devices, Sunnyvale, Calif.) was used for the functional identification of the ligand activating HEK-293 cells expressing (stable) recombinant GPR-14. The day following transfection, cells were plated in a poly-D-lysine coated 96 well black/clear plates. After 18–24 hours the media was aspirated and Fluo 3 AM-loaded cells were exposed to various concentrations (10 nM to 30 uM) of test compounds followed by h-U-II. After initiation of the assay, fluorescence was read every second for one minute and then every 3 seconds for the following one minute. The inhibitory concentration at 50% (IC50)was calculated for various test compounds.

Inositol Phosphates Assays:

HEK-293-GPR14 cells in T150 flask were prelabeled overnight with 1 uCi myo-[$^3$H] inositol per ml of inositol free Dulbecco's modified Eagel's medium. After labeling, the cells were washed twice with Dulbecco's phosphate-buffered saline (DPBS) and then incubated in DPBS containing 10 mM LiCl for 10 min at 37° C. The experiment was initiated by the addition of increasing concentrations of h-U-II (1 pM to 1 μM ) in the absence and presence of three different concentrations (0.3, 1 and 10 uM) of test compounds and the incubation continued for an additional 5 min at 37° C. after which the reaction was terminated by the addition of 10% (final concentration) trichloroacetic acid and centrifugation. The supernatants were neutralized with 100 ul of 1M Trizma base and the inositol phosphates were separated on AG 1-X8 columns (0.8 ml packed, 100–200 mesh) in formate phase. Inositol monophosphate was eluted with 8 ml of 200 mM ammonium formate. Combined inositol di and tris phosphate was eluted with 4 ml of 1M ammonium formate/0.1 M formic acid. Eluted fractions were counted in beta scintillation counter. Based on shift from the control curve K$_B$ was calculated.

Activity for the compounds of this invention range from (radioligand binding assay): Ki=1 nM–10000 nM (example 10,Ki=270 nM).

The following Examples are illustrative but not limiting embodiments of the present invention.

EXAMPLE 1

(R)-N-[4-Chloro-3-(1-methyl-3-pyrrolidinyloxy)-phenyl]-2,4,5-triimethoxybenzenesulfonamide hydrochloride

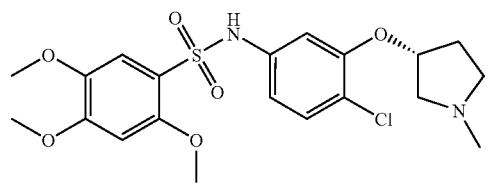

a) 2-Chloro-5-nitrophenol

2-Chloro-5-nitroanisole (310 g, 1.7 mol) was taken up in a mixture of 48% HBr (1.5 L) and AcOH (1.2 L) and heated at reflux for 3 days. The dark solution was allowed to cool to room temperature, poured into ice water (10 L), and let stand for 3 h. The resultant dull yellow solid was filtered, washed with water, and dried in vacuo (230 g, 79%): mp 115–117° C.

b) 2-Chloro-5-aminophenol

A solution of 2-chloro-5-nitrophenol (114 g, 0.66 mol) in ethyl acetate (500 mL) was treated with 5% Pt/C (510 mg, 0.5 weight %) and the mixture shaken under a hydrogen atmosphere (30 psi) for 6 h. The mixture was filtered through Celites® and the residue washed well with ethyl acetate. Evaporation of the ethyl acetate gave a solid (95 g, 100% crude yield) which was taken directly into the next step.

c) 4-Chloro-3-hydroxyphenylcarbamic acid tert-butyl ester

To a solution of 2-chloro-5-aminophenol (95 g, 0.66 mol) in THF (600 mL) was added a solution of di-tert-butyl dicarbonate (144 g, 0.66 mol) in THF (600 mL). The reaction was heated at reflux for 6 h, at which time it was allowed to cool to room temperature. The solvent was removed in vacuo and the residue diluted with ether (1000 mL) and washed with 1 M citric acid (2×1000 mL). The aqueous washings were extracted with ether (500 mL) and the combined organics washed with brine (500 mL), dried (MgSO$_4$), and concentrated. The resultant brown solid was triturated with hexanes and dried in vacuo to give 125 g (78%) of the title compound: mp 103–106° C.

d) 4-Chloro-3-((R)-1-methyl-pyrrolidin-3-yloxy)aniline

To a cooled (0° C.) solution of 4-chloro-3-hydroxyphenylcarbamic acid tert-butyl ester (55 g, 0.23 mol), (S)-1-methyl-pyrrolidin-3-ol (24 g, 0.24 mol), and triphenylphosphine (89 g, 0.34 mol) in THF (1.1 L) was added dropwise via addition funnel a solution of DIAD (67 mL, 0.34 mol) in THF (100 mL) over 1 h. The resultant solution was allowed to slowly warm to ambient temperature and maintained for 16 h. The THF was removed in vacuo and the residue treated with 6 N HCl (650 mL). The resultant mixture was stirred at room temperature for 4 h, at which time it was diluted with water (500 mL) and the filtered to remove the triphenylphosphine oxide. The filtrate was washed with EtOAc (3×1 L) and chloroform (5×1 L) to remove additional reaction by-products. The aqueous layer was then basified with solid NaOH pellets and extracted with ether (2×1 L) and EtOAc (2×1 L). The combined organic layers were washed with saturated NaHCO₃ (2×1 L) and brine (1 L), dried (MgSO₄), and concentrated to give 40 g (80%) of the title compound: MS (ES+) m/e [M+H]⁺227.

e) (R)-N-[4-Chloro-3-(1-methyl-3-pyrrolidinyloxy)-phenyl]-2,4,5-triimethoxybenzenesulfonamide hydrochloride (R)-3-(1-Methyl-3-pyrrolidinyl)-4-chloroaniline (56 mg, 0.25 mmol) was dissolved in dichloroethane (4 mL). 2,4,5-trimethoxybenzenesulfonyl chloride (66 mg, 0.25 mmol) was added and the mixture was allowed to stir at room temperature for 2 days. The mixture was concentrated and the residue recrystallized from ethanol to furnish the title compound (85 mg, 69%): MS (ES+) m/e [M+H]⁺ 457.

EXAMPLE 2a

2-Bromo-4.5-dimethoxybenzenesulfonyl chloride

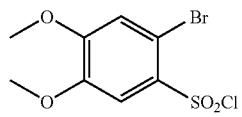

To a cooled (0° C.) solution of 4-bromoveratrole (15 mL, 100 mmol) in dichloromethane (100 mL) was added dropwise chlorosufonic acid (26 mL, 400 mmol). The reaction was allowed to slowly warm to ambient temperature and maintained for 3 hours, at which time it was concentrated and diluted with ether (300 mL). The resultant solution was then washed with ice cold water (2×250 mL) and brine (100 mL), dried over magnesium sulfate, and concentrated to furnish a grayish powder (25 g, 78%).

Examples 15a, 16a, 44a, 47a, 48a, 49a, 50a, 51a, and 1a were made as set forth in Example 2a by substituting the appropriate starting materials.

| Example | Compound |
|---|---|
| 15a | 2-Chloro-4,5-dimethoxy-benzenesulfonyl chloride |
| 16a | 4,5-Dimethoxy-2-methyl-benzenesulfonyl chloride |
| 44a | 4-bromo-2,6-dimethyl-benzenesulfonyl chloride |
| 47a | 4,5-Dimethoxy-2-trifluoromethyl-benzenesulfonyl chloride |
| 48a | 3,5-Difluoro-4-methoxy-2-methyl-benzenesulfonyl chloride |
| 49a | 6-Bromo-2,3-difluoro-4-methoxy-benzenesulfonyl chloride |
| 50a | 4,5-Dimethoxy-2-trifluoromethyl-benzenesulfonyl chloride |
| 51a | 2,6-Dichloro-4,5-dimethoxy-benzenesulfonyl chloride |
| 1a | 2,4,5-Trimethoxy-benzenesulfonyl chloride |

EXAMPLE 2

(R2-Bromo-N-[4-chloro-3-((R)-1-methyl-pyrrolidin-3-yloxy)-phenyl]-4,5-dimethoxybenzenesulfonamide

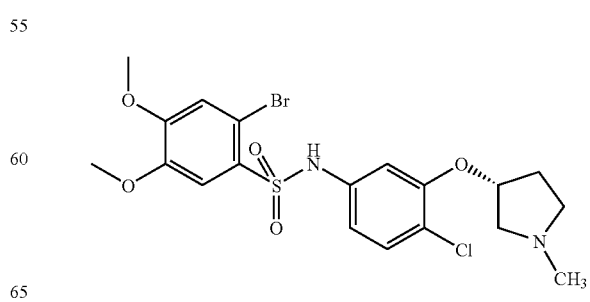

a) 4-Chloro-3-((R)-1-methyl-pyrrolidin-3-yloxy)aniline

4-Chloro-3-((R)-1-methyl-pyrrolidin-3-yloxy)aniline was prepared according to the procedure in 1(a)–(d).

b) 2-Bromo-N-[4-chloro-3-((R)-1-methyl-pyrrolidin-3-yloxy)-phenyl]-4,5-dimethoxybenzenesulfonamide To a solution of 4-chloro-3-((R)-1-methyl-pyrrolidin-3-yloxy) aniline (30 g, 132 mmol) in 1,2-dichloroethane (500 mL) was added a solution of 2-bromo-4,5-dimethoxybenzenesulfonyl chloride (42 g, 135 mmol) in 1,2-dichloroethane (300 mL). The resultant solution was maintained at ambient temperature for 14 h, at which time the solids that had formed were filtered, washed with dichloromethane and ether, and dried in vacuo (50° C.) to afford 58 g (81%) of the title compound: mp 214° C. (dec); MS (ES+) m/e [M+H]$^+$ 505.

Examples 3–53 were made as set forth in Example 1 by substituting the appropriate starting materials.

| Example | Compound | MS (ES+) m/e [M + H]$^+$ |
|---|---|---|
| 3 | (±)-N-[4-Chloro-3-(1-methyl-3-pyrrolidinyloxy)-phenyl]-2-bromo-4,5-dimethoxybenzenesulfonamide | 506 |
| 4 | (±)-N-[4-Chloro-3-(1-ethyl-3-pyrrolidinyloxy)-phenyl]-3,4-dimethoxybenzenesulfonamide | 441 |
| 5 | (S)-N-[4-Chloro-3-(1-methyl-3-pyrrolidinyloxy)-phenyl]-3,4-dimethoxybenzenesulfonamide | 427 |
| 6 | (R)-N-[4-Chloro-3-(1-methyl-3-pyrrolidinyloxy)-phenyl]-3,4-dimethoxybenzenesulfonamide | 427 |

-continued

| Example | Compound | MS (ES+) m/e [M + H]+ |
|---|---|---|
| 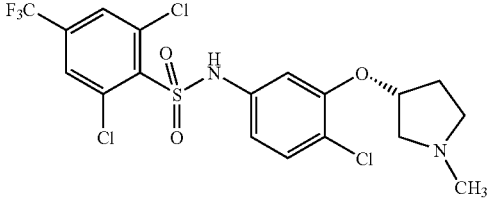<br>7 | (R)-N-[4-Chloro-3-(1-methyl-3-pyrrolidinyloxy)-phenyl]-2,6-dichloro-4-trifluoromethylbenzene-sulfonamide | 503 |
| 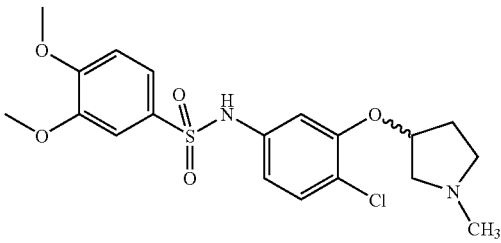<br>8 | (±)-N-[4-Chloro-3-(1-methyl-3-pyrrolidinyloxy)-phenyl]-3,4-dimethoxybenzenesulfonamide | 427 |
| 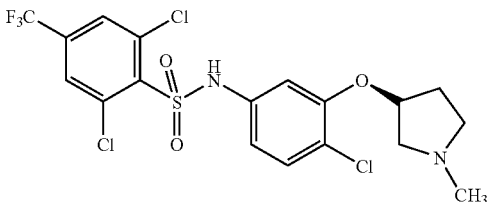<br>9 | (S)-N-[4-Chloro-3-(1-methyl-3-pyrrolidinyloxy)-phenyl]-2,6-dichloro-4-trifluoromethylbenzene-sulfonamide | 503 |
| Chiral<br>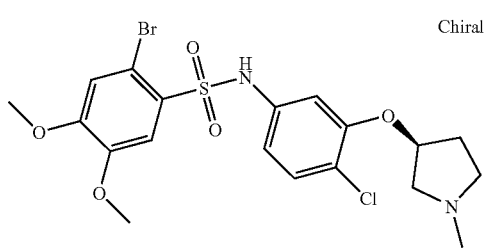<br>10 | 2-Bromo-N-[4-chloro-3-((S)-1-methyl-pyrrolidin-3-yloxy)-phenyl]-4,5-dimethoxy-benzenesulfonamide | 506 |
| Chiral<br>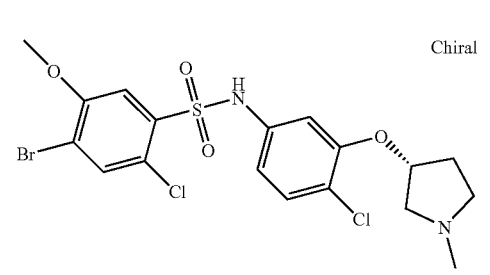<br>11 | 4-Bromo-2-chloro-N-[4-chloro-3-((R)-1-methyl-pyrrolidin-3-yloxy)-phenyl]-5-methoxy-benzenesulfonamide | 510 |

-continued

| Example | | Compound | MS (ES+) m/e [M + H]+ |
|---|---|---|---|
| 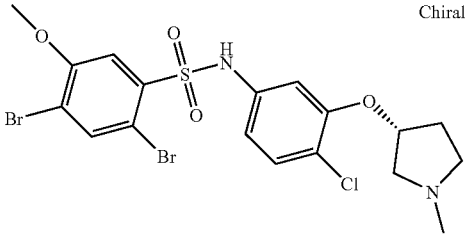 12 | Chiral | 2,4-Dibromo-N-[4-chloro-3-((R)-1-methyl-pyrrolidin-3-yloxy)-phenyl]-5-methoxy-benzenesulfonamide | 555 |
| 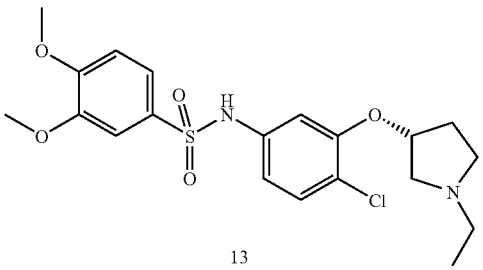 13 | | (R)-N-[4-Chloro-3-(1-ethyl-3-pyrrolidinyloxy)-phenyl]-3,4-dimethoxybenzenesulfonamide | 441 |
| 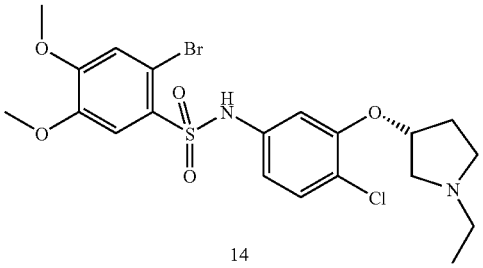 14 | | (R)-N-[4-Chloro-3-(1-ethyl-3-pyrrolidinyloxy)-phenyl]-2-bromo-4,5-dimethoxybenzenesulfonamide | 520 |
| 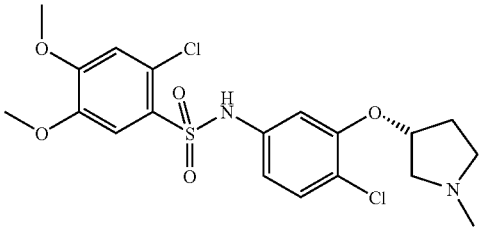 15 | | (R)-N-[4-Chloro-3-(1-methyl-3-pyrrolidinyloxy)-phenyl]-2-chloro-4,5-dimethoxybenzenesulfonamide | 461 |
| 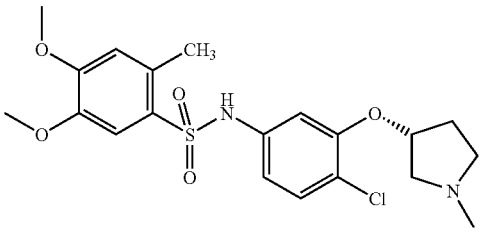 16 | | (R)-N-[4-Chloro-3-(1-methyl-3-pyrrolidinyloxy)-phenyl]-2-methyl-4,5-dimethoxybenzenesulfonamide | 441 |

| Example | Compound | MS (ES+) m/e [M + H]+ |
|---|---|---|
| 17 | (±)-N-[4-Chloro-3-(1-isopropyl-3-pyrrolidinyloxy)-phenyl]-3,4-dimethoxybenzenesulfonamide | 455 |
| 18 | (±)-N-[4-Chloro-3-(1-isopropyl-3-pyrrolidinyloxy)-phenyl]-2-bromo-4,5-dimethoxybenzenesulfonamide | 534 |
| 19 | (R)-N-[4-Chloro-3-(1-isopropyl-3-pyrrolidinyloxy)-phenyl]-2-bromo-4,5-dimethoxybenzenesulfonamide | 534 |
| 20 | (R)-N-[4-Chloro-3-(1-methyl-3-pyrrolidinyloxy)-phenyl]-2-methyl-4-bromobenzenesulfonamide | 460 |
| 21 | (R)-N-[4-Chloro-3-(1-isopropyl-3-pyrrolidinyloxy)-phenyl]-3,4-dimethoxybenzenesulfonamide | 455 |

-continued

| Example | Compound | MS (ES+) m/e [M + H]+ |
|---|---|---|
| 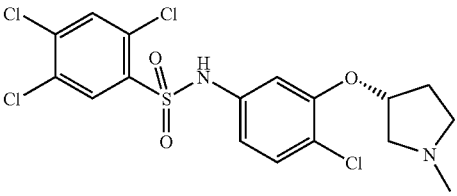<br>22 | (R)-N-[4-Chloro-3-(1-methyl-3-pyrrolidinyloxy)-phenyl]-2,4,5-trichlorobenzenesulfonamide | 469 |
| 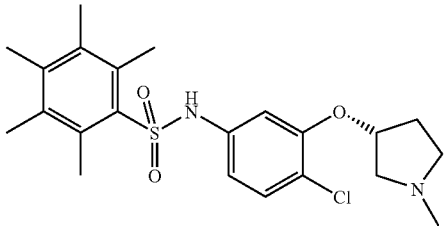<br>23 | (R)-N-[4-Chloro-3-(1-methyl-3-pyrrolidinyloxy)-phenyl]-2,3,4,5,6-pentamethylbenzenesulfonamide | 437 |
| 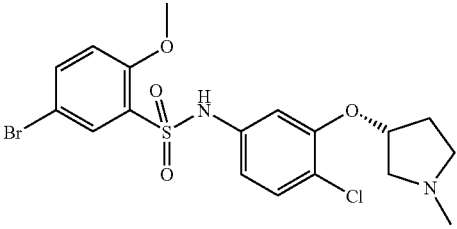<br>24 | (R)-N-[4-Chloro-3-(1-methyl-3-pyrrolidinyloxy)-phenyl]-2-methoxy-5-bromobenzene-sulfonamide | 476 |
| 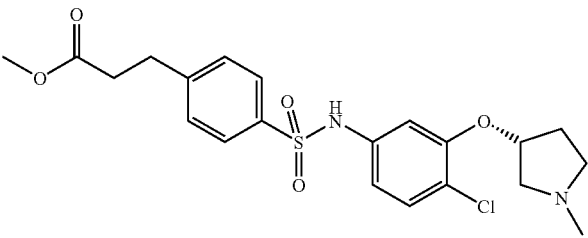<br>25 | (R)-N-[4-Chloro-3-(1-methyl-3-pyrrolidinyloxy)-phenyl]-4-(methylpropionate)benzene-sulfonamide | 453 |
| 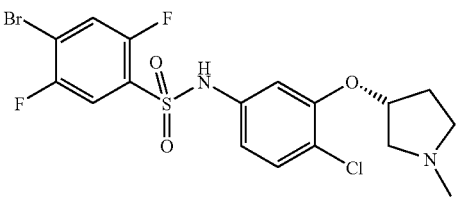<br>26 | (R)-N-[4-Chloro-3-(1-methyl-3-pyrrolidinyloxy)-phenyl]-2,5-difluoro-4-bromobenzene-sulfonamide | 482 |

| Example | Compound | MS (ES+) m/e [M + H]+ |
|---|---|---|
| 27 | (R)-N-[4-Chloro-3-(1-methyl-3-pyrrolidinyloxy)-phenyl]-2,3,6-trimethyl-4-methoxybenzene-sulfonamide | 439 |
| 28 | (R)-N-[4-Chloro-3-(1-methyl-3-pyrrolidinyloxy)-phenyl]-2,3,4-trichlorobenzenesulfonamide | 469 |
| 29 | (R)-N-[4-Chloro-3-(1-methyl-3-pyrrolidinyloxy)-phenyl]-2,3,5,6-tetramethylbenzenesulfonamide | 423 |
| 30 | (R)-N-[4-Chloro-3-(1-methyl-3-pyrrolidinyloxy)-phenyl]-4-isopropylbenzenesulfonamide | 409 |
| 31 | (R)-N-[4-Chloro-3-(1-methyl-3-pyrrolidinyloxy)-phenyl]-4-ethylbenzenesulfonamide | 395 |

-continued

| Example | Compound | MS (ES+) m/e [M + H]+ |
|---|---|---|
| 32 | (R)-N-[4-Chloro-3-(1-methyl-3-pyrrolidinyloxy)-phenyl]-2-chloro-4-cyanobenzenesulfonamide | 426 |
| 33 | (R)-N-[4-Chloro-3-(1-methyl-3-pyrrolidinyloxy)-phenyl]-2,4-dichloro-6-methylbenzene-sulfonamide | 449 |
| 34 | (R)-N-[4-Chloro-3-(1-methyl-3-pyrrolidinyloxy)-phenyl]-2,5-difluoro-3,6-dibromobenzene-sulfonamide | 561 |
| 35 | (R)-N-[4-Chloro-3-(1-methyl-3-pyrrolidinyloxy)-phenyl]-2-trifluoromethoxy-4-bromobenzene-sulfonamide | 460 |
| 36 | (R)-N-[4-Chloro-3-(1-methyl-3-pyrrolidinyloxy)-phenyl]-3-fluorobenzenesulfonamide | 385 |

-continued

| Example | Compound | MS (ES+) m/e [M + H]+ |
|---|---|---|
| 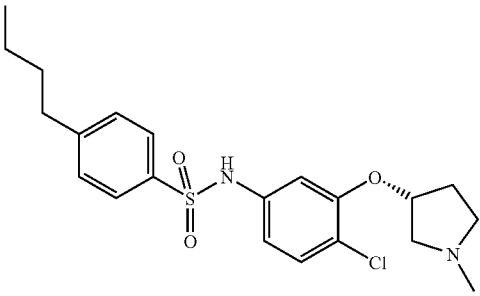<br>37 | (R)-N-[4-Chloro-3-(1-methyl-3-pyrrolidinyloxy)-phenyl]-4-butylbenzenesulfonamide | 423 |
| 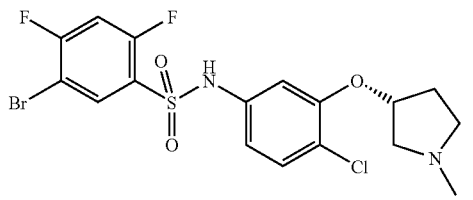<br>38 | (R)-N-[4-Chloro-3-(1-methyl-3-pyrrolidinyloxy)-phenyl]-2,4-difluoro-5-bromobenzene-sulfonamide | 482 |
| 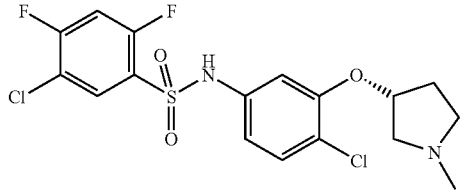<br>39 | (R)-N-[4-Chloro-3-(1-methyl-3-pyrrolidinyloxy)-phenyl]-2,4-difluoro-5-chlorobenzene-sulfonamide | 437 |
| 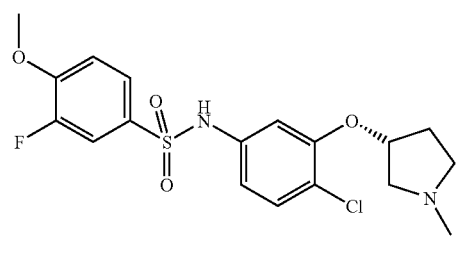<br>40 | (R)-N-[4-Chloro-3-(1-methyl-3-pyrrolidinyloxy)-phenyl]-3-fluoro-4-methoxybenzenesulfonamide | 415 |
| 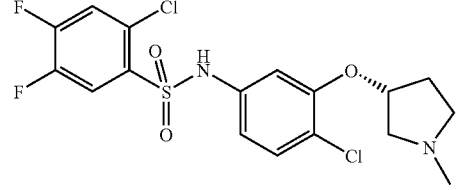<br>41 | (R)-N-[4-Chloro-3-(1-methyl-3-pyrrolidinyloxy)-phenyl]-2-chloro-4,5-difluorobenzenesulfonamide | 437 |

-continued

| Example | Compound | MS (ES+) m/e [M + H]+ |
|---|---|---|
| 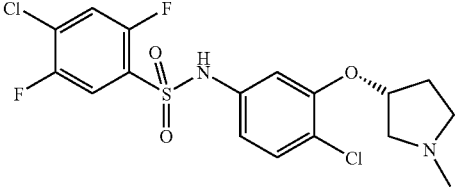<br>42 | (R)-N-[4-Chloro-3-(1-methyl-3-pyrrolidinyloxy)-phenyl]-2,5-difluoro-4-chlorobenzene-sulfonamide | 437 |
| 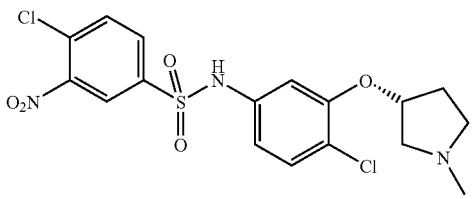<br>43 | (R)-N-[4-Chloro-3-(1-methyl-3-pyrrolidinyloxy)-phenyl]-3-nitro-4-chlorobenzenesulfonamide | 446 |
| 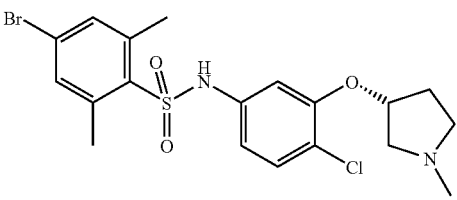<br>44 | (R)-N-[4-Chloro-3-(1-methyl-3-pyrrolidinyloxy)-phenyl]-2,6-dimethyl-4-bromobenzene-sulfonamide | 474 |
| 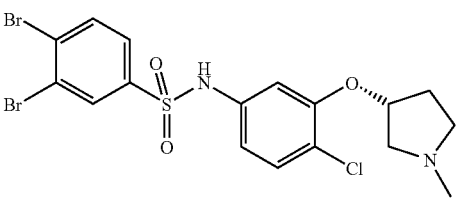<br>45 | (R)-N-[4-Chloro-3-(1-methyl-3-pyrrolidinyloxy)-phenyl]-3,4-dibromobenzenesulfonamide | 525 |
| 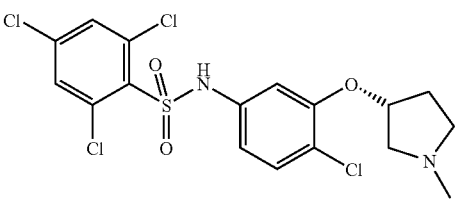<br>46 | (R)-N-[4-Chloro-3-(1-methyl-3-pyrrolidinyloxy)-phenyl]-2,4,6-trichlorobenzenesulfonamide | 469 |
| 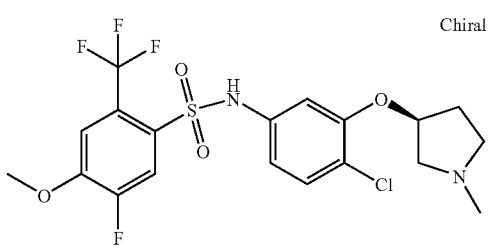<br>Chiral<br>47 | (R)-N-[4-Chloro-3-(1-methyl-3-pyrrolidinyloxy)-phenyl]-5-fluoro-4-methoxy-2-trifluoromethyl-benzenesulfonamide | 483 |

-continued

| Example | Compound | MS (ES+) m/e [M + H]+ |
|---|---|---|
| 48 Chiral | (R)-N-[4-Chloro-3-(1-methyl-3-pyrrolidinyloxy)-phenyl]-3,5-difluoro-4-methoxy-2-methyl-benzenesulfonamide | 447 |
| 49 Chiral | (R)-N-[4-Chloro-3-(1-methyl-3-pyrrolidinyloxy)-phenyl]-6-bromo-2,3-difluoro-4-methoxy-benzenesulfonamide | 512 |
| 50 Chiral | (R)-N-[4-Chloro-3-(1-methyl-3-pyrrolidinyloxy)-phenyl]-4,5-dimethoxy-2-trifluoromethyl-benzenesulfonamide | 495 |
| 51 Chiral | (R)-N-[4-Chloro-3-(1-methyl-3-pyrrolidinyloxy)-phenyl]-2,6-dichloro-4,5-dimethoxy-benzenesulfonamide | 495 |
| 52 Chiral | (R)-N-[4-Chloro-3-(1-methyl-3-pyrrolidinyloxy)-phenyl]-4-fluoro-2-trifluoromethyl-benzenesulfonamide | 453 |
| 53 Chiral | (R)-N-[4-Chloro-3-(1-methyl-3-pyrrolidinyloxy)-phenyl]-2,4,6-trifluoro-benzenesulfonamide | 421 |

EXAMPLES 54–59

Substituting 5-amino-o-cresol for 2-chloro-5-aminophenol and substituting various sulfonyl chlorides for 2,4,5-trimethoxybenzenesulfonyl chloride, examples 54–59 were prepared following the procedures described in 1c–1e:

| Example | Compound | MS (ES+) m/e [M + H]⁺ |
|---|---|---|
| 54 | Chiral 3,4-Dimethoxy-N-[4-methyl-3-((R)-1-methyl-pyrrolidin-3-yloxy)-phenyl]-benzenesulfonamide | 407 |
| 55 | Chiral 2-Bromo-4,5-dimethoxy-N-[4-methyl-3-((R)-1-methyl-pyrrolidin-3-yloxy)-phenyl]-benzenesulfonamide | 486 |
| 56 | Chiral 2-Chloro-4,5-dimethoxy-N-[4-methyl-3-((R)-1-methyl-pyrrolidin-3-yloxy)-phenyl]-benzenesulfonamide | 441 |
| 57 | Chiral 4,5-Dimethoxy-2-methyl-N-[4-methyl-3-((R)-1-methyl-pyrrolidin-3-yloxy)-phenyl]-benzenesulfonamide | 421 |
| 58 | Chiral 4-Bromo-2-chloro-5-methoxy-N-[4-methyl-3-((R)-1-methyl-pyrrolidin-3-yloxy)-phenyl]-benzenesulfonamide | 490 |

| Example | Compound | MS (ES+) m/e [M + H]+ |
|---|---|---|
| 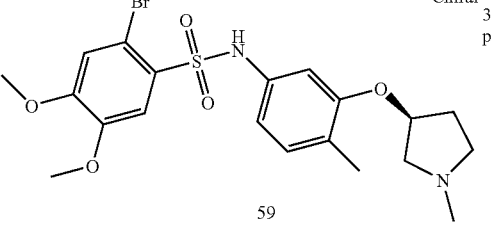  59 | Chiral 2-Bromo-4,5-dimethoxy-N-[4-methyl-3-((S)-1-methyl-pyrrolidin-3-yloxy)-phenyl]-benzenesulfonamide | 486 |

EXAMPLE 60

N-[4-Chloro-3-((R)-pyrrolidin-3-yloxy)-phenyl]-2-bromo-3,4-dimethoxybenzenesulfonamide

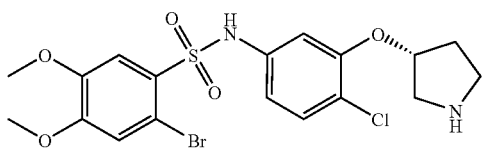

a) (R)-3(5-amino-2-chlorophenoxy)-pyrrolidine

To solution of (R)-3-(5-tert-butoxycarbonylamino-2-chlorophenoxy)-pyrrolidine-1-carboxylic acid-tert-butyl ester (2 g, 4.9 mmol) in dioxane (30 mL) was added 6 N hydrogen chloride (20 mL). The reaction mixture was stirred for 2 hours, at which time it was concentrated. The resultant residue was triturated with ethyl acetate and dichloromethane, the diluted with 2.5 M potassium hydroxide (50 mL) and extracted with dichloromethane (3×50 mL). The combined organics were washed with brine (50 mL), dried over magnesium sulfate, and concentrated to give (R)-3-(5-amino-2-chlorophenoxy)-pyrrolidine (810 mg, 75%).

b) (R)-3-(5-amino-2-chlorophenoxy)-pyrrolidine-1-carboxylic acid-tert-butyl ester To a solution of (R)-3-(5-amino-2-chlorophenoxy)-pyrrolidine (810 mg, 3.9 mmol) in tetrahydrofuran (40 mL) was added di-tert-butyl-dicarbonate (830 mg, 3.9 mmol). The resultant solution was maintained at ambient temperature for 20 hours, at which time it was diluted with ether (100 mL), washed with 5% aqueous citric acid (100 mL), water (100 mL), and brine (50 mL), and dried over magnesium sulfate. Concentration of the solution gave (R)-3-(5-amino-2-chlorophenoxy)-pyrrolidine-1-carboxylic acid-tert-butyl ester (1.2 g, 99%).

c) N-[4-Chloro-3-((R)-pyrrolidin-3-yloxy)-phenyl]-2-bromo-3,4-dimethoxybenzenesulfonamide To a solution of (R)-3-(5-amino-2-chlorophenoxy)-pyrrolidine-1-carboxylic acid-tert-butyl ester (100 mg, 0.33 mmol) in chloroform (5 mL) was added 2-bromo-4,5-dimethoxybenzenesulfonyl chloride (120 mg, 0.33 mmol). The resultant solution was maintained at ambient temperature for 24 hours, at which time it was concentrated. The residue was diluted with dioxane (4 mL) and 6 N hydrogen chloride (2 mL) and stirred for 5 hours, at which time it was concentrated. Crystallization from ethanol furnished the title compound (22 mg, 11%). MS (ES+) m/e 492 [M+H]+

Using the appropriate starting materials, the following compounds were made according to example 60.

| Example | Compound | MS (ES+) m/e [M + H]+ |
|---|---|---|
| 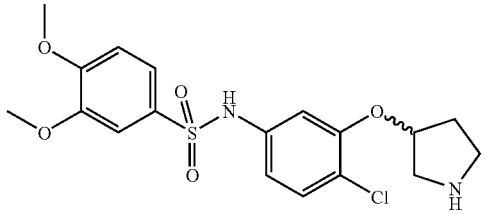  61 | (±)-N-[4-Chloro-3-(3-pyrrolidinyloxy)-phenyl]-3,4-dimethoxybenzenesulfonamide | 413 |

| Example | Compound | MS (ES+) m/e [M + H]+ |
|---|---|---|
| 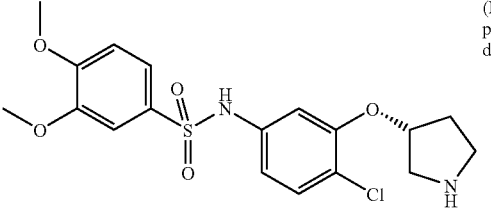 62 | (R)-N-[4-Chloro-3-(3-pyrrolidinyloxy)-phenyl]-3,4-dimethoxybenzenesulfonamide | 413 |
| 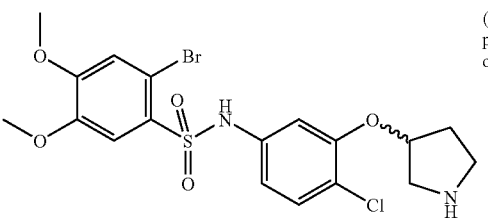 63 | (±)-N-[4-Chloro-3-(3-pyrrolidinyloxy)-phenyl]-2-bromo-4,5-dimethoxybenzenesulfonamide | 492 |

EXAMPLE 64

2-Bromo-4,5-dimethoxy-N-[3-(1-methyl-pyrrolidin-3-yloxy-4-trifluormethy-phenyl]-benzenesulfonamide

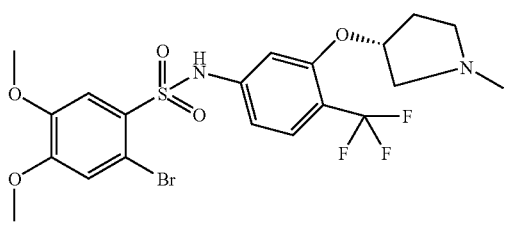

a) 2-Fluoro-4-nitrobenzotrifluoride

A solution of 4-amino-2-fluorobenzotrifluoride (25.0 g, 0.14 mol, 1.0 eq) in trifluoroacetic acid (140 ml) was heated to reflux then was treated with the dropwise addition of 50% hydrogen peroxide (66.7 ml, 1.18 mol, 8.4 eq) over 35 min. The reaction was heated at reflux for 1.5 hrs further then cooled to ambient temperature. Poured into ice-water (1 L) then stirred overnight. The oil that separated was collected (decanting the water phase) then diluted with diethyl ether (150 ml). The ether solution was washed with aqueous 10% HCl (100 ml), saturated aqueous sodium bicarbonate (2×100 ml), and brine (100 ml) then dried over anhydrous magnesium sulphate. Evaporation under reduced pressure gave an orange-brown oil. Distillation (14 torr, 88–90° C.) gave the product as a yellow liquid (15.0 g, 51%)

b) 2-((R)-1-Methyl-pyrrolidin-3-yloxy)-4-nitrobenzotrifluoride

A solution of 2-fluoro-4-nitrobenzotrifluoride (12.4 g, 59.3 mmol, 1.0 eq) and (R)-1-methyl-pyrrolidin-3-ol (6.0 g, 59.3 mmol, 1.0 eq) in anhydrous tetrahydrofuran (150 ml) was cooled to 0° C. then slowly treated with portions of 60% sodium hydride (4.7 g, 0.12 mol, 2 eq) over 5 min. Without removing the ice bath, the reaction was allowed to come to room temperature and stir for 48 hrs. Quenched with water (50 ml) and brine (100 ml) then extracted into diethyl ether (5×100 ml). Extracts dried over anhydrous magnesium sulfate and decolorizing charcoal for 1 hr. Filtered through Celite. The filtrate was treated with silica (35 g) then evaporated to give the crude product suspended on silica. Column chromatography on silica (1% MeOH/EtOAc→5% MeOH/EtOAc) gave the product (Rf≅0.3 in 1% MeOH/EtOAc) as an orange oil (7.85 g, 46%).

c) 3-((R)-1-Methyl-pyrrolidin-3-yloxy)-4-trifluoromethyl-phenylamine

A solution of 2-((R)-1-Methyl-pyrrolidin-3-yloxy)-4-nitrobenzotrifluoride (7.8 g, 26.9 mmol) in ethyl acetate (50 ml) was treated with 10% platinum on carbon (200 mg) then subjected to 40 psi hydrogen pressure for 3 hrs. The slurry was treated with anhydrous magnesium sulfate (5 g) then filtered through a pad of Celite. The filter cake was rinsed with ethyl acetate (2×25 ml) then the filtrate was evaporated under reduced pressure to an oil. This oil was evaporated twice for dichloromethane (50 ml) to remove trapped ethyl acetate. This gave the product as a clear light brown oil that solidified on standing (6.9 g, 99%): LCMS 249 (M++H).

d) 2-Bromo-4,5-dimethoxy-N-[3-((R)-1-methyl-pyrrolidin-3-yloxy)-4-trifluoromethyl-phenyl]-benzenesulfonamide A solution of 3-((R)-1-methyl-pyrrolidin-3-yloxy)-4-trifluoromethyl-phenylamine (250 mg, 0.96 mmol) and 2-bromo-4,5-dimethoxybenzenesulfonyl chloride (303 mg, 0.96 mmol) in anhydrous 1,2-dichloroethane (5 ml) was stirred at ambient temperature for 3 days. The reaction mixture was evaporated under reduced pressure to a gum, then taken into dimethylsulfoxide (3 ml) and purified by preparative HPLC. The combined fractions were evaporated under reduced pressure to give the product as the TFA salt.

This was treated with aqueous 10% NaOH (50 ml) and methylene chloride (50 ml). The resulting suspension was stirred vigorously for 20 min, then filtered to collect the insoluble product free base. The dried free base was dissolved into methanol (5 ml) then treated with concentrated hydrochloric acid (0.1 ml). Evaporation under reduced pressure gave the product hydrochloride salt as a pale yellow solid (347 mg, 63%): MS (ES+) m/e [M+H]$^+$ 539.

EXAMPLES 65–85

Substituting 3-((R)-1-methyl-pyrrolidin-3-yloxy)-4-trifluoromethyl-phenylamine for (R)-3-(1-methyl-3-pyrrolidinyl)-4-chloroaniline and substituting various sulfonyl chlorides for 2,4,5-trimethoxybenzenesulfonyl chloride, examples 65–85 were prepared following the procedure described in 1e

| Example | | Compound | MS (ES+) m/e [M + H]$^+$ |
|---|---|---|---|
| 65 | Chiral | 2-Chloro-4,5-dimethoxy-3-[((R)-1-methyl-pyrrolindin-3-yloxy)-4-trifluoromethyl-phenyl]-benzenesulfonamide | 495 |
| 66 | | 2,6-Dichloro-[3-((R)-1-methyl-pyrrolidin-3-yloxy)-4-trifluoromethyl-phenyl]-4-trifluoromethyl-benzenesulfonamide | 537 |
| 67 | Chiral | 3,4-Dimethoxy-N-[3-((R)-1-methyl-pyrrolidin-3-yloxy)-4-trifluoromethyl-phenyl]-benzenesulfonamide | 461 |
| 68 | Chiral | 2,4,5-Trichloro-N-[3-((R)-1-methyl-pyrrolidin-3-yloxy)-4-trifluoromethyl-phenyl]-benzenesulfonamide | 503 |

-continued

| Example | | Compound | MS (ES+) m/e [M + H]+ |
|---|---|---|---|
|  69 | Chiral | 2,3,4,5,6-Pentamethyl-N-[3-((R)-1-methyl-pyrrolidin-3-yloxy)-4-trifluoromethyl-phenyl]-benzenesulfonamide | 471 |
|  70 | Chiral | 4-Bromo-2,5-difluoro-N-[3-((R)-1-methyl-pyrrolidin-3-yloxy)-4-trifluoromethyl-phenyl]-benzenesulfonamide | 516 |
|  71 | Chiral | 2,3,4-Trichloro-N-[3-((R)-1-methyl-pyrrolidin-3-yloxy)-4-trifluoromethyl-phenyl]-benzenesulfonamide | 503 |
|  72 | Chiral | 4-Isopropyl-N-[3-((R)-1-methyl-pyrrolidin-3-yloxy)-4-trifluoromethyl-phenyl]-benzenesulfonamide | 443 |

-continued

| Example | | Compound | MS (ES+) m/e [M + H]+ |
|---|---|---|---|
| 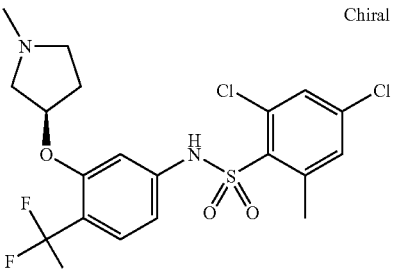 73 | Chiral | 2,4-Dichloro-6-methyl-N-[3-((R)-1-methyl-pyrrolidin-3-yloxy)-4-trifluoromethyl-phenyl]-benzenesulfonamide | 483 |
| 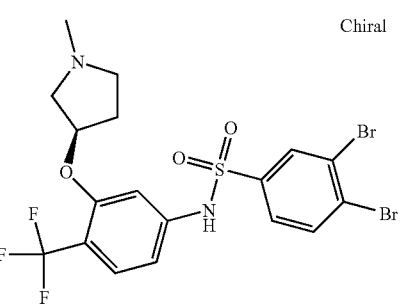 74 | Chiral | 3,4-Dibromo-N-[3-((R)-1-methyl-pyrrolidin-3-yloxy)-4-trifluoromethyl-phenyl]-benzenesulfonamide | 559 |
| 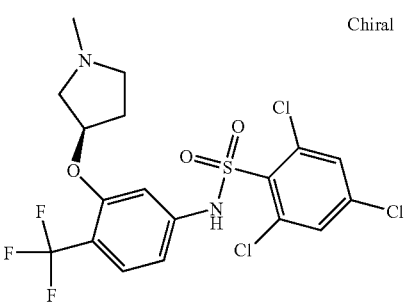 75 | Chiral | 2,4,6-Trichloro-N-[3-((R)-1-methyl-pyrrolidin-3-yloxy)-4-trifluoromethyl-phenyl]-benzenesulfonamide | 503 |
| 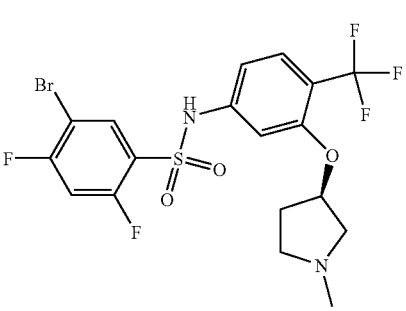 76 | Chiral | 5-Bromo-2,4-difluoro-N-[3-((R)-1-methyl-pyrrolidin-3-yloxy)-4-trifluoromethyl-phenyl]-benzenesulfonamide | 516 |

| Example | | Compound | MS (ES+) m/e [M + H]+ |
|---|---|---|---|
| 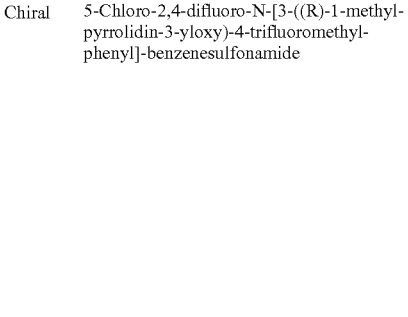<br>77 | Chiral | 5-Chloro-2,4-difluoro-N-[3-((R)-1-methyl-pyrrolidin-3-yloxy)-4-trifluoromethyl-phenyl]-benzenesulfonamide | 471 |
| 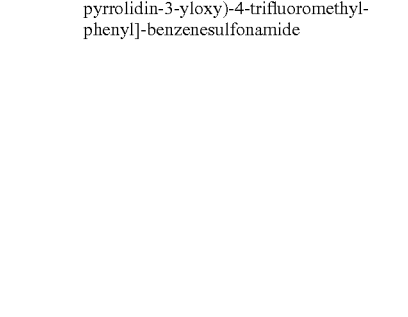<br>78 | Chiral | 4-Chloro-2,5-difluoro-N-[3-((R)-1-methyl-pyrrolidin-3-yloxy)-4-trifluoromethyl-phenyl]-benzenesulfonamide | 471 |
| 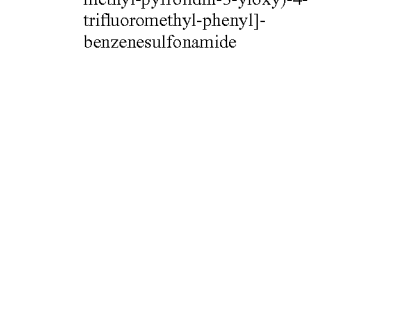<br>79 | Chiral | 4-Methoxy-2,3,6-trimethyl-N-[3-((R)-1-methyl-pyrrolidin-3-yloxy)-4-trifluoromethyl-phenyl]-benzenesulfonamide | 473 |
| 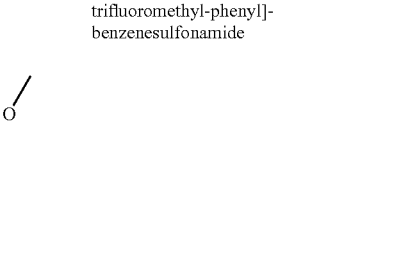<br>80 | Chiral | 3,5-Dimethoxy-2-methyl-N-[3-((R)-1-methyl-pyrrolidin-3-yloxy)-4-trifluoromethyl-phenyl]-benzenesulfonamide | 475 |

-continued

| Example | Compound | MS (ES+) m/e [M + H]+ |
|---|---|---|
| 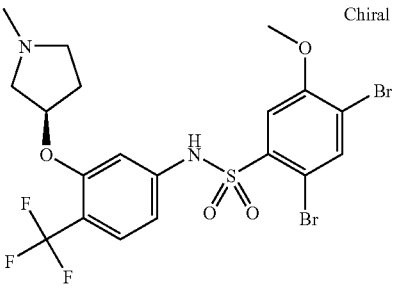 81 | 2,4-Dibromo-5-methoxy-N-[3-((R)-1-methyl-pyrrolidin-3-yloxy)-4-trifluoromethyl-phenyl]-benzenesulfonamide | 589 |
| 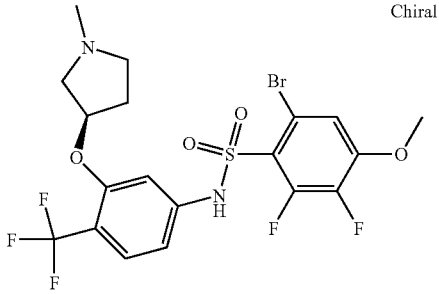 82 | 2-Bromo-5,6-difluoro-4-methoxy-N-[3-((R)-1-methyl-pyrrolidin-3-yloxy)-4-trifluoromethyl-phenyl]-benzenesulfonamide | 546 |
| 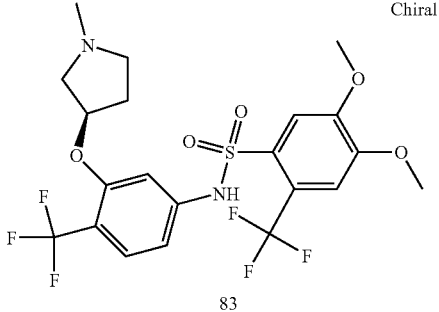 83 | 4,5-Dimethoxy-2-trifluoromethyl-N-[3-((R)-1-methyl-pyrrolidin-3-yloxy)-4-trifluoromethyl-phenyl]-benzenesulfonamide | 529 |
| 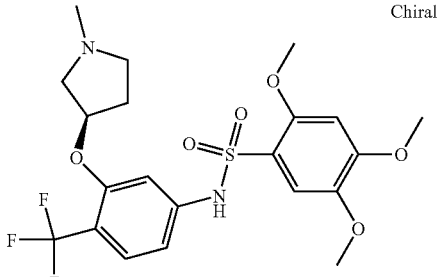 84 | 2,4,5-Trimethoxy-N-[3-((R)-1-methyl-pyrrolidin-3-yloxy)-4-trifluoromethyl-phenyl]-benzenesulfonamide | 491 |

| Example | Compound | MS (ES+) m/e [M + H]+ |
|---|---|---|
| 85 Chiral | 4-Bromo-2,6-dimethyl-N-[3-((R)-1-methyl-pyrrolidin-3-yloxy)-4-trifluoromethyl-phenyl]-benzenesulfonamide | 508 |

EXAMPLE 86

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

Procedure for tablets:

Step 1: Blend ingredients No. 1, No. 2, No. 3 and No. 4 in a suitable mixer/blender.

Step 2: Add sufficient water portion-wise to the blend from Step 1 with careful mixing after each addition. Such additions of water and mixing until the mass is of a consistency to permit its conversion to wet granules.

Step 3: The wet mass is converted to granules by passing it through an oscillating granulator using a No. 8 mesh (2.38 mm) screen.

Step 4: The wet granules are then dried in an oven at 140° F. (60° C.) until dry.

Step 5: The dry granules are lubricated with ingredient No. 5.

Step 6: The lubricated granules are compressed on a suitable tablet press.

Inhalant Formulation

A compound of Formula I, (1 mg to 100 mg) is aerosolized from a metered dose inhaler to deliver the desired amount of drug per use.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound of Formula (I):

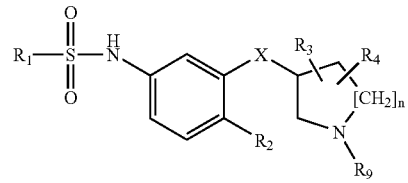

Formula (I)

wherein:

$R^1$ is phenyl substituted or unsubstituted by one, two, three, four or five of any of the following:

halogen, $CF_3$, $OCF_3$, $SCF_3$, $NO_2$, CN, $C_{1-6}$ alkyl, $C_{1-6}$ alkoxy, $NR_5R_6$, $CONR_7R_8$, $SC_{1-6}$ alkyl, $CO_2(C_{1-6}$ alkyl), or $C_{1-6}$ alkyl-$CO_2(C_{1-6}$ alkyl);

$R_2$ is hydrogen, halogen, $CF_3$, CN or $C_{1-4}$ alkyl;

$R_3$, $R_4$, $R_7$, and $R_8$ are independently hydrogen, $C_{1-6}$ alkyl, or benzyl;

$R_5$, $R_6$, and $R_9$, are independently hydrogen or $C_{1-6}$ alkyl;

X is O, S, or $CH_2$;

n is 1;

or a pharmaceutically acceptable salt thereof.

2. A compound according to claim 1 wherein $R^1$ is phenyl substituted or unsubstituted by one, two, three, four, or five of any of the following: halogen, $CF_3$, $OCF_3$, CN, $C_{1-6}$ alkyl, $C_{1-6}$ alkoxy, $CO_2(C_{1-6}$ alkyl), $C_{1-6}$ alkyl-$CO_2(C_{1-6}$ alkyl), or $NO_2$; $R_2$ is hydrogen, halogen, $CF_3$, or $C_{1-4}$ alkyl; $R_3$ is hydrogen; $R_4$ is hydrogen; $R_9$ is hydrogen or $C_{1-6}$ alkyl; and X is O.

3. A compound according to claim 1 wherein $R_1$ is phenyl substituted or unsubstituted by one, two, three or four of the following: halogen, CF$_3$, CN, methyl, methoxy; R$_2$ is halogen or CF$_3$, R$_3$ is hydrogen; R$_4$ is hydrogen; R$_9$ is hydrogen or C$_{1-6}$ alkyl; and X is O.

4. A compound according to claim 1 chosen from the group consisting of:
- (R)-N-[4-Chloro-3-(1-methyl-3-pyrrolidinyloxy)-phenyl]-2,4,5-triimethoxy-benzenesulfonamide hydrochloride;
- (±)-N-[4-Chloro-3-(1-methyl-3-pyrrolidinyloxy)-phenyl]-2-bromo-4,5-dimethoxybenzenesulfonamide;
- (±)-N-[4-Chloro-3-(1-ethyl-3-pyrrolidinyloxy)-phenyl]-3,4-dimethoxybenzenesulfonamide;
- (S)-N-[4-Chloro-3-(1-methyl-3-pyrrolidinyloxy)-phenyl]-3,4-dimethoxybenzenesulfonamide;
- (R)-N-[4-Chloro-3-(1-methyl-3-pyrrolidinyloxy)-phenyl]-3,4-dimethoxybenzenesulfonamide;
- (R)-N-[4-Chloro-3-(1-methyl-3-pyrrolidinyloxy)-phenyl]-2-bromo-4,5-dimethoxybenzenesulfonamide;
- (R)-N-[4-Chloro-3-(1-methyl-3-pyrrolidinyioxy)-phenyl]-2,6-dichloro-4-trifluoromethylbenzenesulfonamide;
- (±)-N-[4-Chloro-3-(1-methyl-3-pyrrolidinyloxy)-phenyl]-3,4-dimethoxybenzenesulfonamide;
- (S)-N-[4-Chloro-3-(1-methyl-3-pyrrolidinyloxy)-phenyl]-2,6-dichloro-4-trifluoromethylbenzenesulfonamide;
- 2-Bromo-N-[4-chloro-3-((S)-1-methyl-pyrrolidin-3-yloxy)-phenyl]-4,5-dimethoxybenzenesulfonamide;
- 4-Bromo-2-chloro-N-[4-chloro-3-((R)-1-methyl-pyrrolidin-3-yloxy)-phenyl]-5-methoxybenzenesulfonamide;
- 2,4-Dibromo-N-[4-chloro-3-((R)-1-methyl-pyrrolidin-3-yloxy)-phenyl]-5-methoxybenzenesulfonamide;
- (R)-N-[4-Chloro-3-(1-ethyl-3-pyrrolidinyloxy)-phenyl]-3,4-dimethoxybenzenesulfonamide;
- (R)-N-[4-Chloro-3-(1-ethyl-3-pyrrolidinyloxy)-phenyl]-2-bromo-4,5-dimethoxybenzenesulfonamide;
- (R)-N-[4-Chloro-3-(1-methyl-3-pyrrolidinyloxy)-phenyl]-2-chloro-4,5-dimethoxybenzenesulfonamide;
- (R)-N-[4-Chloro-3-(1-methyl-3-pyrrolidinyloxy)-phenyl]-2-methyl-4,5-dimethoxybenzenesulfonamide;
- (±)-N-[4-Chloro-3-(1-isopropyl-3-pyrrolidinyloxy)-phenyl]-3,4-dimethoxybenzenesulfonamide;
- (±)-N-[4-Chloro-3-(1-isopropyl-3-pyrrolidinyloxy)-phenyl]-2-bromo-4,5-dimethoxybenzenesulfonamide;
- (R)-N-[4-Chloro-3-(1-isopropyl-3-pyrrolidinyloxy)-phenyl]-2-bromo-4,5-dimethoxybenzenesulfonamide;
- (R)-N-[4-Chloro-3-(1-methyl-3-pyrrolidinyloxy)-phenyl]-2-methyl-4-bromobenzenesulfonamide;
- (R)-N-[4-Chloro-3-(1-isopropyl-3-pyrrolidinyloxy)-phenyl]-3,4-dimethoxybenzenesulfonamide;
- (R)-N-[4-Chloro-3-(1-methyl-3-pyrrolidinyloxy)-phenyl]-2,4,5-trichlorobenzenesulfonamide;
- (R)-N-[4-Chloro-3-(1-methyl-3-pyrrolidinyloxy)-phenyl]-2,3,4,5,6-pentamethylbenzenesulfonamide;
- (R)-N-[4-Chloro-3-(1-methyl-3-pyrrolidinyloxy)-phenyl]-2-methoxy-5-bromobenzenesulfonamide;
- (R)-N-[4-Chloro-3-(1-methyl-3-pyrrolidinyloxy)-phenyl]-4-(methylpropionate)benzenesulfonamide;
- (R)-N-[4-Chloro-3-(1-methyl-3-pyrrolidinyloxy)-phenyl]-2,5-difluoro-4-bromobenzenesulfonamide;
- (R)-N-[4-Chloro-3-(1-methyl-3-pyrrolidinyloxy)-phenyl]-2,3,6-trimethyl-4-methoxybenzenesulfonamide;
- (R)-N-[4-Chloro-3-(1-methyl-3-pyrrolidinyloxy)-phenyl]-2,3,4-trichlorobenzenesulfonamide;
- (R)-N-[4-Chloro-3-(1-methyl-3-pyrrolidinyloxy)-phenyl]-2,3,5,6-tetramethylbenzenesulfonamide;
- (R)-N-[4-Chloro-3-(1-methyl-3-pyrrolidinyioxy)-phenyl]-4-isopropylbenzenesulfonamide;
- (R)-N-[4-Chloro-3-(1-methyl-3-pyrrolidinyloxy)-phenyl]-4-ethylbenzenesulfonamide;
- (R)-N-[4-Chloro-3-(1-methyl-3-pyrrolidinyloxy)-phenyl]-2-chloro-4-cyanobenzenesusfonamide;
- (R)-N-[4-Chloro-3-(1-methyl-3-pyrrolidinyioxy)-phenyl]-2,4-dichloro-6-methylbenzenesulfonamide;
- (R)-N-[4-Chloro-3-(1-methyl-3-pyrrolidinyloxy)-phenyl]-2,5-difluoro-3,6-dibromobenzenesulfonamide;
- (R)-N-[4-Chloro-3-(1-methyl-3-pyrrolidinyloxy)-phenyl]-2-trifluoromethoxy-4-bromobenzenesulfonamide;
- (R)-N-[4-Chloro-3-(1-methyl-3-pyrrolidinyloxy)-phenyl]-3-fluorobenzenesulfonamide;
- (R)-N-[4-Chloro-3-(1-methyl-3-pyrrolidinyloxy)-phenyl]-4-butylbenzenesulfonamide;
- (R)-N-[4-Chloro-3-(1-methyl-3-pyrrolidinyloxy)-phenyl]-2,4-difluoro-5-bromobenzenesulfonamide;
- (R)-N-[4-Chloro-3-(1-methyl-3-pyrrolidinyloxy)-phenyl]-2,4-difluoro-5-chlorobenzenesulfonamide;
- (R)-N-[4-Chloro-3-(1-methyl-3-pyrrolidinyloxy)-phenyl]-3-fluoro-4-methoxybenzenesulfonamide;
- (R)-N-[4-Chloro-3-(1-methyl-3-pyrrolidinyloxy)-phenyl]-2-chloro-4,5-difluorobenzenesulfonamide;
- (R)-N-[4-Chloro-3-(1-methyl-3-pyrrolidinyloxy)-phenyl]-2,5-difluoro-4-chlorobenzenesulfonamide;
- (R)-N-[4-Chloro-3-(1-methyl-3-pyrrolidinyloxy)-phenyl]-3-nitro-4-chlorobenzenesulfonamide;
- (R)-N-[4-Chloro-3-(1-methyl-3-pyrrolidinyloxy)-phenyl]-2,6-dimethyl-4-bromobenzenesulfonamide;
- (R)-N-[4-Chloro-3-(1-methyl-3-pyrrolidinyloxy)-phenyl]-3,4-dibromobenzenesulfonamide;
- (R)-N-[4-Chloro-3-(1-methyl-3-pyrrolidinyloxy)-phenyl]-2,4,6-trichlorobenzenesulfonamide;
- (R)-N-[4-Chloro-3-(1-methyl-3-pyrrolidinyloxy)-phenyl]-5-fluoro-4-methoxy-2-trifluoromethylbenzenesulfonamide;
- (R)-N-[4-Chloro-3-(1-methyl-3-pyrrolidinyloxy)-phenyl]-3,5-difluoro-4-methoxy-2-methylbenzenesulfonamide;
- (R)-N-[4-Chloro-3-(1-methyl-3-pyrrolidinyloxy)-phenyl]-6-bromo-2,3-difluoro-4-methoxybenzenesulfonamide;
- (R)-N-[4-Chloro-3-(1-methyl-3-pyrrolidinyloxy)-phenyl]-4,5-dimethoxy-2-trifluoromethylbenzenesulfonamide;
- (R)-N-[4-Chloro-3-(1-methyl-3-pyrrolidinyloxy)-phenyl]-2,6-dichloro-4,5-dimethoxybenzenesulfonamide;
- (R)-N-[4-Chloro-3-(1-methyl-3-pyrrolidinyloxy)-phenyl]-4-fluoro-2-trifluoromethylbenzenesulfonamide;
- (R)-N-[4-Chloro-3-(1-methyl-3-pyrrolidinyloxy)-phenyl]-2,4,6-trifluoro-benzenesulfonamide;
- 3,4-Dimethoxy-N-[4-methyl-3-((R)-1-methyl-pyrrolidin-3-yloxy)-phenyl]-benzenesulfonamide;
- 2-Bromo-4,5-dimethoxy-N-[4-methyl-3-((R)-1-methyl-pyrrolidin-3-yloxy)-phenyl]-benzenesulfonamide;
- 2-Chloro-4,5-dimethoxy-N-[4-methyl-3-((R)-1-methyl-pyrrolidin-3-yloxy)-phenyl]-benzenesulfonamide;
- 4,5-Dimethoxy-2-methyl-N-[4-methyl-3-((R)-1-methyl-pyrrolidin-3-yloxy)-phenyl]-benzenesulfonamide;
- 4-Bromo-2-chloro-5-methoxy-N-[4-methyl-3-((R)-1-methyl-pyrrolidin-3-yloxy)-phenyl]-benzenesulfonamide;
- 2-Bromo-4,5-dimethoxy-N-[4-methyl-3-((S)-1-methyl-pyrrolidin-3-yloxy)-phenyl]-benzenesulfonamide;
- N-[4-Chloro-3-((R)-pyrrolidin-3yloxy)-phenyl]-2-bromo-3,4-dimethoxy-benzenesulfonamide;

(±)-N-[4-Chloro-3-(3-pyrrolidinyloxy)-phenyl]-3,4-dimethoxybenzenesulfonamide;
(R)-N-[4-Chloro-3-(3-pyrrolidinyloxy)-phenyl]-3,4-dimethoxybenzenesulfonamide;
(±)-N-[4-Chloro-3-(3-pyrrolidinyloxy)-phenyl]-2-bromo-4,5-dimethoxybenzenesulfonamide;
2-Chloro-4,5-dimethoxy-3-[((R)- 1-methyl-pyrrolindin-3-yloxy)-4-trifluoromethyl-phenyl]-benzenesulfonamide;
2,6-Dichloro-[3-((R)-1-methyl-pyrrolidin-3-yloxy)-4-trifluoromethyl-phenyl]-4-trifluoromethyl -benzenesulfonamide;
2-Bromo-4,5-dimethoxy-N-[3-(1-methyl-pyrrolidin-3-yloxy-4-trifluormethy-phenyl]-benzenesulfonamide;
3,4-Dimethoxy-N-[3-((R)-1-methyl-pyrrolidin-3-yloxy)-4-triftuoromethyl-phenyl]-benzenesulfonamide;
2,4,5-Trichloro-N-[3-((R)-1-methyl-pyrrolidin-3-yloxy)-4-trifluoromethyl-phenyl]-benzenesulfonamide;
2,3,4,5,6-Pentamethyl-N-[3-((R)-1-methyl-pyrrolidin-3-yloxy)-4-trifluoromethyl-phenyl]-benzenesulfonamide;
4-Bromo-2,5-difluoro-N-[3-((R)-1-methyl-pyrrolidin-3-yloxy)-4-trifluoromethyl-phenyl]-benzenesulfonamide;
2,3,4-Trichloro-N-[3-((R)-1-methyl-pyrrolidin-3-yloxy)-4-trifluoromethyl-phenyl]-benzenesulfonamide;
4-Isopropyl-N-[3-((R)-1-methyl-pyrrolidin-3-yloxy)-4-trifluoromethyl-phenyl]-benzenesulfonamide;
2,4-Dichloro-6-methyl-N-[3-((R)-1-methyl-pyrrolidin-3-yloxy)-4-trifluoromethyl-phenyl]-benzenesulfonamide;
3,4-Dibromo-N-[3-((R)- 1-methyl-pyrrolidin-3-yloxy)-4-trifluoromethyl-phenyl]-benzenesulfonamide;
2,4,6-Trichloro-N-[3-((R)-1-methyl-pyrrolidin-3-yloxy)-4-trifluoromethyl-phenyl]-benzenesulfonamide;
5-Bromo-2,4-difluoro-N-[3-((R)-1-methyl-pyrrolidin-3-yloxy)-4-trifluoromethyl-phenyl]-benzenesulfonamide;
5-Chloro-2,4-difluoro-N-[3-((R)- 1-methyl-pyrrolidin-3-yloxy)-4-trifluoromethyl-phenyl]-benzenesulfonamide;
4-Chloro-2,5-difluoro-N-[3-((R)- 1-methyl-pyrrolidin-3-yloxy)-4-trifluoromethyl-phenyl]-benzenesulfonamide;
4-Methoxy-2,3,6-trimethyl-N-[3-((R)- 1-methyl-pyrrolidin-3-yloxy)-4-trifluoromethyl-phenyl]-benzenesulfonamide;
3,5-Dimethoxy-2-methyl-N-[3-((R)-1-methyl-pyrrolidin-3-yloxy)-4-trifluoromethyl-phenyl]-benzenesulfonamide;
2,4-Dibromo-5-methoxy-N-[3-((R)-1-methyl-pyrrolidin-3-yloxy)-4-trifluoromethyl-phenyl]-benzenesulfonamide;
2-Bromo-5,6-difluoro-4-methoxy-N-[3-((R)-1-methyl-pyrrolidin-3-yloxy)-4-trifluoromethyl -phenyl]-benzenesulfonamide;
4,5-Dimethoxy-2-trifluoromethyl-N-[3-((R)-1-methyl-pyrrolidin-3-yloxy)-4-trifluoromethyl-phenyl]-benzenesulfonamide;
2,4,5-Trimethoxy-N-[3-((R)-1-methyl-pyrrolidin-3-yloxy)-4-trifluoromethyl-phenyl]-benzenesulfonamide; and
4-Bromo-2,6-dimethyl-N-[3-((R)- 1-methyl-pyrrolidin-3-yloxy)-4-trifluoromethyl-phenyl]-benzenesulfonamide.

5. A compound according to claim 1 chosen from the group consisting of:
(R)-N-[4-Chloro-3-(1-methyl-3-pyrrolidinyloxy)-phenyl]-2-bromo-4,5-dimethoxybenzenesulfonamide;
(R)-N-[4-Chloro-3-(1-methyl-3-pyrrolidinyloxy)-phenyl]-2,6-dichloro-4-trifluoromethylbenzenesulfonamide;
(R)-N-[4-Chloro-3-(1-methyl-3-pyrrolidinyloxy)-phenyl]-2-chloro-4,5-dimethoxybenzenesulfonamide;
(R)-N-[4-Chloro-3-(1-methyl-3-pyrrolidinyloxy)-phenyl]-2,3,6-trimethyl-4-methoxybenzenesulfonamide;
2-Bromo-4,5-dimethoxy-N-[3-((R)- 1-methyl-pyrrolidin-3-yloxy)-.4-trifluoromethyl-phenyl]-benzenesulfonamide;
2-Chloro-4,5-dimethoxy-N-[3-((R)-1-methyl-pyrrolidin-3-yloxy)-4-trifluoromethyl-phenyl]-benzenesulfonamide; and
2,6-Dichloro-[3-((R)-1-methyl-pyrrolidin-3-yloxy)-4-trifluoromethyl-phenyl]-4-trifluoromethylbenzenesulfonamide.

6. A compound of claim 1 chosen from:
2-Bromo-4,5-di methoxy-N-[3-((R)-1-methyl-pyrrolidin-3-yloxy)-4-trifluoromethyl-phenyl]-benzenesulfonamide; and
2-Bromo-N-[4-chloro-3-((R)- 1-methyl-pyrrolidin-3-yloxy)-phenyl]-4,5-dimethoxybenzenesulfonamide.

7. A pharmaceutical composition comprising a compound of formula (I) of claim 1 and a pharmaceutically acceptable carrier or excipient.

8. A pharmaceutical composition comprising a compound of formula (I) of claim 5 and a pharmaceutically acceptable carrier or excipient.

9. A method of treating congestive heart failure, stroke, ischemic heart disease, angina, myocardial ischemia, cardiac arrhythmia, essential and pulmonary hypertension, renal disease, acute and chronic renal failure, end stage renal disease, peripheral vascular disease, male erectile dysfunction, diabetic retinopathy, intermittent claudication/ischemic limb disease, ischemic/hemorrhagic stroke, COPD, restenosis, asthma, neurogenic inflammation, migraine, metabolic vasculopathies, bone/cartilage/joint diseases, arthritis, fibrosis, pulmonary fibrosis, sepsis, atherosclerosis, dyslipidemia, addiction, schizophrenia, Alzheimers disease, impulsivity, anxiety, stress, depression, parkinsons, sleep-wake cycle, incentive motivation, pain, neuromuscular function, diabetes, gastric reflux, and ulcers which comprises administering to a patient in need thereof, a compound of Formula I of claim 1.

10. A process for the preparation of a compound of Formula (I) of claim 1 or a pharmaceutically acceptable salt thereof, which process comprises hydrogenation of a compound of Formula (II)

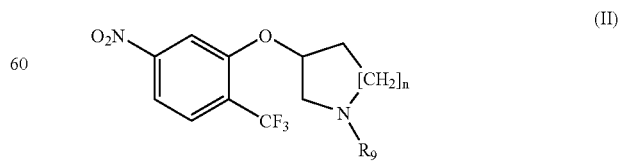

(II)

wherein $R_9$ and n are as described in claim 1, or a group convertible thereto, to give a compound of Formula (Ill)

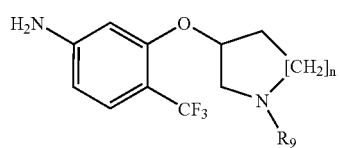 (III)
which is reacted with a compound of Formula (IV)
R₁—SO₂Cl (IV)
wherein $R_1$ is as described in claim 1, or a group convertible thereto,
and when desired or necessary, conversion of $R_1$ and/or $R_9$;
to afford a compound of Formula (I).
* * * * *